(12) United States Patent
Kleemann et al.

(10) Patent No.: US 7,531,663 B2
(45) Date of Patent: May 12, 2009

(54) 3-GUANIDINOCARBONYL-1-HETEROARYL-INDOLE DERIVATIVES, PREPARATION PROCESS, THEIR USE AS MEDICAMENTS, AND PHARMACEUTICAL COMPOSITIONS COMPRISING THEM

(75) Inventors: Heinz-Werner Kleemann, Bischofsheim (DE); Jean-Christophe Carry, Saint Maur des Fosses (FR); Pascal Desmazeau, Tigery (FR); Serge Mignani, Chatenay-Malabry (FR); Jean Bouquerel, Drancy (FR); Arielle Genevois-Borella, Thiais (FR); Baptiste Ronan, Clamart (FR)

(73) Assignee: sanofi-aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/749,630

(22) Filed: Dec. 31, 2003

(65) Prior Publication Data

US 2005/0026989 A1    Feb. 3, 2005

Related U.S. Application Data

(63) Continuation of application No. PCT/EP03/07024, filed on Jul. 2, 2003.

(51) Int. Cl.
*C07D 215/38* (2006.01)
(52) U.S. Cl. ..................................... 546/167; 548/454
(58) Field of Classification Search ................ 514/412, 514/314; 546/167; 548/454
See application file for complete search history.

(56) References Cited

U.S. PATENT DOCUMENTS 5,852,046 A    12/1998   Lang et al.

FOREIGN PATENT DOCUMENTS

| EP | 0622356 | 11/1994 |
| EP | 0 708 091 | * 4/1996 |
| WO | WO 95/22524 | 8/1995 |
| WO | WO 99/43663 | 9/1999 |
| WO | WO 00/71537 | 11/2000 |

OTHER PUBLICATIONS

Everett, Chris, Haemolytic disease of the newborn—time to prevent unnecessary deaths, Comparative Medicine, The British Journal of General Practice, 2000, 50 (5), p. 511.
Howitz, et al., Uber 0, p- und ana-Jodchinolin und deren Derivate, Justus Liebigs Ann. Chem. (1913), 396, pp. 53-75.
Schultheis, Patrick, et al., Targeted Disruption of the Murine Na+/H+ Exchanger Isoform 2 Gene Causes Reduced Viability of Gastric Parietal Cells and Loss of Net Acid Secretion, J. Clin. Invest., 1998, 101 (6), pp. 1243-1253.
Sui, Z. et, al., A Convenient Synthesis of 3,5-Bis(Trifluoromethyl) Salicylic Acid, Synthetic Communications, 1997, 27(20), pp. 3581-3590.
Toyota, Masahiro, et al. , Tandem Michael Addition-[3.3] Sigmatropic Rearrangement Processes, Part 2. Constuction of Cyclopropa [3,4] pyrrolo [3,2-e] indol-4-one (CPI) Unit of Antitumour Antibiotic CC-1065, J. Chem. Soc. Perkin Trans. 1, (1992), (5), pp. 547-552.

* cited by examiner

*Primary Examiner*—D. Margaret Seaman
(74) *Attorney, Agent, or Firm*—James W. Bolcsak

(57) ABSTRACT

The present invention relates to 3-guanidinocarbonyl-1-heteroaryl-indole derivatives, pharmaceutical compositions comprising such derivatives, methods of treatment comprising administering such derivatives, and processes for their preparation.

7 Claims, No Drawings

3-GUANIDINOCARBONYL-1-HETEROARYL-INDOLE DERIVATIVES, PREPARATION PROCESS, THEIR USE AS MEDICAMENTS, AND PHARMACEUTICAL COMPOSITIONS COMPRISING THEM

The present invention relates to 3-guanidinocarbonyl-1-heteroaryl-indole derivatives of the formula (I)

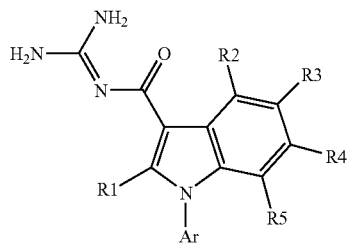

in which R1 to R5 and Ar have the meanings stated below. The inventive compounds are suitable for example as antiarrhythmic medicaments with a cardioprotective component for infarction prophylaxis and infarction treatment and for the treatment of angina pectoris. They also inhibit in a preventive manner the pathophysiological processes associated with the development of ischemia-induced damage, in particular in the triggering of ischemia-induced cardiac arrhythmias and of heart failure.

The invention relates to compounds of the formula I, in which

R1 is hydrogen or alkyl having 1, 2, 3, 4, 5 or 6 carbon atoms,
R2 is hydrogen, alkyl having 1, 2, 3, 4, 5 or 6 carbon atoms, halogen, NRaRb or polyfluoroalkyl having 1, 2, 3 or 4 carbon atoms,
Ra and Rb
  are independently of each other hydrogen, linear or branched alkyl having 1, 2, 3, 4, 5 or 6 carbon atoms or Ra and Rb form, together with the nitrogen atom to which they are attached, a 5- or 6-membered heterocycle, which may optionally contain another hetero atom chosen from O, S and N,
R3 is hydrogen, alkyl having 1, 2, 3, 4, 5 or 6 carbon atoms, halogen, alkoxy having 1, 2, 3, 4, 5 or 6 carbon atoms or hydroxyl,
R4 is hydrogen, alkyl having 1, 2, 3, 4, 5 or 6 carbon atoms, halogen, alkoxy having 1, 2, 3, 4, 5 or 6 carbon atoms or hydroxyl,
R5 is hydrogen or halogen,
R3 is hydrogen, alkyl having 1, 2, 3, 4, 5 or 6 carbon atoms, halogen, alkoxy having 1, 2, 3, 4, 5 or 6 carbon atoms or hydroxyl,
R4 is hydrogen, alkyl having 1, 2, 3, 4, 5 or 6 carbon atoms, halogen, alkoxy having 1, 2, 3, 4, 5 or 6 carbon atoms or hydroxyl,
R5 is hydrogen or halogen,
Ar is a 9- or a 10-membered bicyclic heteroaryl having one, two or three nitrogen atoms, which may be linked via any of its positions, and racemic mixtures, enantiomers and diastereomers thereof and mixtures thereof, tautomers thereof and pharmaceutically acceptable salts thereof.

Preference is given to compounds of the formula I, in which

R1 is hydrogen or alkyl having 1, 2, 3, 4, 5 or 6 carbon atoms,
R2 is hydrogen, alkyl having 1, 2, 3, 4, 5 or 6 carbon atoms, halogen, NRaRb or polyfluoroalkyl having 1, 2, 3 or 4 carbon atoms,
Ra and Rb
  are independently of each other hydrogen, linear or branched alkyl having 1, 2, 3, 4, 5 or 6 carbon atoms or Ra and Rb form, together with the nitrogen atom to which they are attached, a 5- or 6-membered heterocycle, which may optionally contain another hetero atom chosen from O, S and N,
R3 is hydrogen, alkyl having 1, 2, 3, 4, 5 or 6 carbon atoms, halogen, alkoxy having 1, 2, 3, 4, 5 or 6 carbon atoms or hydroxyl,
R4 is hydrogen, alkyl having 1, 2, 3, 4, 5 or 6 carbon atoms, halogen, alkoxy having 1, 2, 3, 4, 5 or 6 carbon atoms or hydroxyl,
R5 is hydrogen or halogen,
Ar is quinoline, isoquinoline, cinnoline or 7H-pyrrolo-[2,3-d]-pyrimidine, which may be linked via any of its positions, and racemic mixtures, enantiomers and diastereomers thereof and mixtures thereof, tautomers thereof and pharmaceutically acceptable salts thereof.

More preference is given to compounds of the formula I, in which

R1 is hydrogen or alkyl having 1, 2, 3, 4, 5 or 6 carbon atoms,
R2 is hydrogen, alkyl having 1, 2, 3, 4, 5 or 6 carbon atoms, halogen, NRaRb or polyfluoroalkyl having 1, 2, 3, 4, 5 or 6 carbon atoms,
Ra and Rb
  are independently of each other hydrogen, linear or branched alkyl having 1, 2, 3, 4, 5 or 6 carbon atoms or Ra and Rb form, together with the nitrogen atom to which they are attached, a 5- or 6-membered heterocycle, which may optionally contain another hetero atom chosen from O, S and N,
R3 is hydrogen, alkyl having 1, 2, 3, 4, 5 or 6 carbon atoms, halogen, alkoxy having 1, 2, 3, 4, 5 or 6 carbon atoms or hydroxyl,
R4 is hydrogen, alkyl having 1, 2, 3, 4, 5 or 6 carbon atoms, halogen, alkoxy having 1, 2, 3, 4, 5 or 6 carbon atoms or hydroxyl,
R5 is hydrogen or halogen,
Ar is quinoline, which may be linked via any of its positions and racemic mixtures, enantiomers and diastereomers thereof and mixtures thereof, tautomers thereof and pharmaceutically acceptable salts thereof.

Another peference is given to compounds of the formula I, in which

R1 is hydrogen or alkyl having 1, 2, 3, 4, 5 or 6 carbon atoms,
R2 is hydrogen, alkyl having 1, 2, 3, 4, 5 or 6 carbon atoms, halogen, NRaRb or polyfluoroalkyl having 1, 2, 3, 4, 5 or 6 carbon atoms,
Ra and Rb
  are independently of each other hydrogen, linear or branched alkyl having 1, 2, 3, 4, 5 or 6 carbon atoms or Ra and Rb form, together with the nitrogen atom to which they are attached, a 5- or 6-membered heterocycle, which may optionally contain another hetero atom chosen from O, S and N,
R3 is hydrogen, alkyl having 1, 2, 3, 4, 5 or 6 carbon atoms, halogen, alkoxy having 1, 2, 3, 4, 5 or 6 carbon atoms or hydroxyl, R4 is hydrogen, alkyl having 1, 2, 3, 4, 5 or 6 carbon atoms, halogen, alkoxy having 1, 2, 3, 4, 5 or 6 carbon atoms or hydroxyl, R5 is hydrogen or halogen, Ar is isoquinoline, which may be linked via any of its positions and racemic mixtures, enantiomers and diastereomers thereof and mixtures thereof, tautomers thereof and pharmaceutically acceptable salts thereof.

In one embodiment compounds of the formula I are defined as above and R1 represents hydrogen or methyl, preferably hydrogen.

In another embodiment compounds of the formula I are defined as above and R2 represents hydrogen or methyl, preferably hydrogen.

In another embodiment compounds of the formula I are defined as above and R3 and R4 represent independently of each other hydrogen, methyl, chlorine, fluorine or methoxy. Preferably one of R3 and R4 represents hydrogen and the other of R3 and R4 represents methyl, chlorine, fluorine or methoxy.

In another embodiment compounds of the formula I are defined as above and R5 represents hydrogen, fluorine or chlorine, preferably hydrogen.

In another embodiment compounds of the formula I are defined as above and Ar represents quinoline, isoquinoline, quinazoline, cinnoline or 7H-pyrrolo-[2,3-d]-pyrimidine, which may be linked via any of its positions, preferred quinoline, isoquinoline or cinnoline, more preferred 2-quinolinyl, 3-quinolinyl, 4-quinolinyl, 6-quinolinyl, 8-quinolinyl, 1-isoquinolinyl, 3-isoquinolinyl or 4-cinnolinyl, specifically preferred 4-quinolinyl or 1-isoquinolinyl.

Specific preference is given to compounds of the formula I, characterised in that it is chosen from the group of:
3-guanidinocarbonyl-1-(isoquinol-1-yl)-1H-indole,
3-guanidinocarbonyl-1-(quinol-4-yl)-1H-indole,
3-guanidinocarbonyl-1-(quinol-2-yl)-1H-indole,
3-guanidinocarbonyl-1-(isoquinol-1-yl)-5-methyl-1H-indole,
3-guanidinocarbonyl-5-methyl-1-(quinol-2-yl)-1H-indole,
3-guanidinocarbonyl-5-methyl-1-(quinol-4-yl)-1H-indole,
3-guanidinocarbonyl-1-(quinol-3-yl)-1H-indole,
3-guanidinocarbonyl-1-(quinol-6-yl)-1H-indole,
3-guanidinocarbonyl-1-(quinol-8-yl)-1H-indole,
3-guanidinocarbonyl-1-(isoquinol-3-yl)-1H-indole,
3-guanidinocarbonyl-6-methoxy-1-(quinol-4-yl)-1H-indole,
3-guanidinocarbonyl-6-hydroxy-1-(quinol-4-yl)-1H-indole,
6-fluoro-3-guanidinocarbonyl-1-(quinol-4-yl)-1H-indole,
5-fluoro-3-guanidinocarbonyl-1-(quinol-4-yl)-1H-indole,
4-chloro-3-guanidinocarbonyl-1-(quinol-4-yl)-1H-indole,
5-chloro-3-guanidinocarbonyl-1-(quinol-4-yl)-1H-indole,
6-chloro-3-guanidinocarbonyl-1-(quinol-4-yl)-1H-indole,
4-fluoro-3-guanidinocarbonyl-1-(quinol-4-yl)-1H-indole,
3-guanidinocarbonyl-4-methyl-1-(quinol-4-yl)-1H-indole,
3-guanidinocarbonyl-4-trifluoromethyl-1-(quinol-4-yl)-1H-indole,
4-dimethylamino-3-guanidinocarbonyl-1-(quinol-4-yl)-1H-indole,
3-guanidinocarbonyl-1-(cinnolin-4-yl)-1H-indole and
5-methoxy-3-guanidinocarbonyl-1-(cinnolin-4-yl)-1H-indole,
and tautomers thereof and pharmaceutically acceptable salts thereof, and more particularly the following compounds:
3-guanidinocarbonyl-1-(isoquinol-1-yl)-1H-indole,
3-guanidinocarbonyl-1-(quinol-4-yl)-1H-indole,
3-guanidinocarbonyl-1-(quinol-2-yl)-1H-indole,
3-guanidinocarbonyl-1-(isoquinol-1-yl)-5-methyl-1H-indole,
3-guanidinocarbonyl-5-methyl-1-(quinol-2-yl)-1H-indole,
3-guanidinocarbonyl-5-methyl-1-(quinol-4-yl)-1H-indole,
3-guanidinocarbonyl-1-(quinol-3-yl)-1H-indole,
3-guanidinocarbonyl-1-(quinol-6-yl)-1H-indole,
3-guanidinocarbonyl-1-(quinol-8-yl)-1H-indole,
3-guanidinocarbonyl-1-(isoquinol-3-yl)-1H-indole,
3-guanidinocarbonyl-6-methoxy-1-(quinol-4-yl)-1H-indole,
6-fluoro-3-guanidinocarbonyl-1-(quinol-4-yl)-1H-indole,
5-fluoro-3-guanidinocarbonyl-1-(quinol-4-yl)-1H-indole,
5-chloro-3-guanidinocarbonyl-1-(quinol-4-yl)-1H-indole,
3-guanidinocarbonyl-1-(cinnolin-4-yl)-1H-indole and
5-methoxy-3-guanidinocarbonyl-1-(cinnolin-4-yl)-1H-indole, and tautomers thereof and pharmaceutically acceptable salts thereof.

If the inventive compounds contain one or more centers of asymmetry, these may independently of one another have the S and the R configuration. The compounds may be in the form of optical isomers, of diastereomers, of racemates or of mixtures thereof in any ratio.

The present invention encompasses all tautomeric forms of the compounds of the formula I.

Alkyl radicals may be straight-chain or branched. This also applies if they carry substituents or occur as substituents of other radicals, for example in alkylamino, alkoxy or polyfluoroalkyl radicals. Examples of alkyl radicals are methyl, ethyl, n-propyl, isopropyl (=1-methylethyl), n-butyl, isobutyl (=2-methylpropyl), sec-butyl (=1-methylpropyl), tert-butyl (=1,1-dimethylethyl), pentyl or hexyl. Preferred alkyl radicals are methyl, ethyl, n-propyl, isopropyl, tert-butyl and isobutyl. One or more, for example 1, 2, 3, 4, 5, 6, 7, 8 or 9, hydrogen atoms in alkyl radicals may be replaced by fluorine atoms to form polyfluoroalkyl radicals. Examples of such radicals are difluoromethyl, trifluoromethyl, pentafluoroethyl, 2,2,2-trifluoroethyl; 3,3,3-trifluoropropyl, trifluorobutyl. Analogously in alkoxy radicals 1 to 3 carbons can be substituted by 1, 2, 3, 4, 5, 6 or 7 fluorine atoms, for example trifluoromethoxy.

Examples of the group NRaRb in which Ra and Rb form, together with the nitrogen atom to which they are attached, a saturated or unsaturated 5- or 6-membered heterocycle, are piperidin-1-yl, pyrrolidin-1-yl, morpholin-4-yl, thiomorpholin-4-yl or piperazin-1-yl.

9- or 10-membered bicyclic heteroaryl radicals, having one, two or three nitrogen atoms, may be attached by all positions, for example by the 1 position, 2 position, 3 position, 4 position, 5 position, 6 position, 7 position or 8 position. Examples of these unsubstituted heteroaryl radicals are quinoline, isoquinoline, quinazoline, cinnoline, quinoxaline, phthalazine or 7H-pyrrolo-[2,3-d]-pyrimidine, preferably quinoline, isoquinoline, quinazoline, cinnoline or 7H-pyrrolo-[2,3-d]-pyrimidine, more preferably quinoline, isoquinoline or cinnoline.

The halogen radicals are either chlorine, bromine, fluorine or iodine.

As used above, and throughout the description of the invention, the following terms, unless otherwise indicated, shall be understood to have the following meanings.

"Patient" includes both human and other mammals.

"Effective amount" is meant to describe an amount of compound, composition, medicament or other active ingredient effective in producing the desired therapeutic effect.

The compounds of the formula I inhibit the cellular sodium-proton antiporter ($Na^+/H^+$-exchanger, NHE), in particular they inhibit the subtype NHE1. Because of the NHE-inhibitory properties, the compounds of the formula I and/or the pharmaceutically acceptable salts thereof are suitable for the prevention and treatment of diseases caused by activation of or activated NHE, and of diseases caused secondarily by NHE-related damage.

Patent EP 639 573 discloses heteroaroylguanidine derivatives as NHE inhibitors. Specific indole derivatives are disclosed, but no compounds with a bicyclic heteroaryl group in position 1 and with the guanidinocarbonyl in position 3.

Patent EP 622 356 discloses indoloylguanidines with a substituent on the nitrogen of the indole, which is hydrogen or a substituted or unsubstituted alkyl or a cycloalkyl or an OH or an alkoxy.

The compounds of the formula (I) can be used as novel medicaments in the treatment of diseases as inhibitors of NHE and in particular of NHE-1 with good selectivity for NHE-1 with respect to NHE-2. This good selectivity makes it possible to reduce the potential gastrointestinal side effects existing with regard to molecules having inadequate selectivity (J. Clin. Invest., 1998, 101(6), 1243; Comparative Medicine, 2000, 50(5), 511, the content of which is incorporated herein by reference).

Since NHE inhibitors predominantly act via their effect on cellular pH regulation, they can generally be combined beneficially with other compounds which regulate the intracellular pH, with suitable combination partners being, for example, inhibitors of the carbonate dehydratase enzyme group, inhibitors of systems transporting bicarbonate ions, such as of the sodium bicarbonate cotransporter (NBC) or of the sodium-dependent chloride-bicarbonate exchanger (NCBE), and NHE inhibitors with inhibitory effect on other NHE subtypes, because it is possible through them to enhance or modulate the pharmacologically relevant pH-regulating effects of the NHE inhibitors described herein.

The use of the compounds of the invention relates to the prevention and treatment of acute and chronic diseases in veterinary and human medicine, in particular human medicine.

Thus, the NHE inhibitors of the invention are suitable for the treatment of diseases caused by ischemia and by reperfusion.

The compounds described herein are suitable because of their pharmacological properties as antiarrhythmic medicaments.

Owing to their cardioprotective component, the NHE inhibitors of the formula I and/or the pharmaceutically acceptable salts thereof are outstandingly suitable for infarction prophylaxis and infarction treatment and for the treatment of angina pectoris, in which cases they also preventively inhibit or greatly reduce the pathophysiological processes associated with the development of ischemia-induced damage, in particular in the triggering of ischemia-induced cardiac arrhythmias. Because of their protective effects against pathological hypoxic and ischemic situations, the compounds of the formula I and/or the pharmaceutically acceptable salts thereof used according to the invention can, because of inhibition of the cellular $Na^+/H^+$ exchange mechanism, be used as medicaments for the treatment of all acute or chronic ischemia-induced damage or diseases induced primarily or secondarily thereby.

This also relates to their use as medicaments for surgical interventions. Thus, the compounds can be used during organ transplantations, it being possible to use the compounds both to protect the organs in the donor before and during the removal, to protect removed organs for example during treatment with or storage thereof in physiological bath liquids, and during transfer to the recipient organism.

The compounds of the invention are likewise valuable medicaments with a protective effect when performing angioplastic surgical interventions, for example on the heart as well as on peripheral organs and vessels.

It has emerged that the compounds of the invention are exceptionally effective medicaments for life-threatening arrhythmias. Ventricular fibrillation is terminated and the physiological sinus rhythm of the heart is restored.

Since NHE1 inhibitors of human tissue and organs, especially the heart, protect effectively not only against damage caused by ischemia and reperfusion but also against the cytotoxic effect of medicaments like those used in particular in cancer therapy and the therapy of autoimmune diseases, combined administration with compounds of the formula I and/or the pharmaceutically acceptable salts thereof is suitable for inhibiting the cytotoxic, especially cardiotoxic, side effects of said compounds. The reduction in the cytotoxic effects, especially the cardiotoxicity, resulting from comedication with NHE1 inhibitors makes it additionally possible to increase the dose of the cytotoxic therapeutic agents and/or to prolong the medication with such medicaments. The therapeutic benefits of such a cytotoxic therapy can be considerably increased by combination with NHE inhibitors.

In addition, the NHE1 inhibitors of the invention of the formula I and/or the pharmaceutically acceptable salts thereof can be used when there is heart-damaging overproduction of thyroid hormones, thyrotoxicosis, or on external supply of thyroid hormones. The compounds of the formula I and/or the pharmaceutically acceptable salts thereof are thus suitable for improving therapy with cardiotoxic medicaments.

In accordance with their protective effect against ischemia-induced damage, the compounds of the invention are also suitable as medicaments for the treatment of ischemias of the nervous system, especially of the central nervous system, being suitable for example for the treatment of stroke or of cerebral edema.

The compounds of the formula I and/or the pharmaceutically acceptable salts thereof are also suitable for the therapy and prophylaxis of diseases and disorders induced by overexcitability of the central nervous system, in particular for the treatment of epileptic disorders, centrally induced clonic and tonic spasms, states of psychological depression, anxiety disorders and psychoses. In these cases it is possible to use the NHE inhibitors described herein alone or in combination with other substances with antiepileptic activity or antipsychotic active ingredients, or carbonate dehydratase inhibitors, for example with acetazolamide, and with other inhibitors of NHE or of the sodium-dependent chloride-bicarbonate exchanger (NCBE).

The compounds according to the invention of the formula I and/or the pharmaceutically acceptable salts thereof are additionally likewise suitable for the treatment of types of shock such as, for example, of allergic, cardiogenic, hypovolemic and bacterial shock.

The compounds of the formula I and/or the pharmaceutically acceptable salts thereof can likewise be used for the prevention and treatment of thrombotic disorders because they, as NHE inhibitors, are able to inhibit platelet aggregation themselves. They are additionally able to inhibit or prevent the excessive release, occurring after ischemia and reperfusion, of mediators of inflammation and coagulation, especially of von Willebrand factor and of thrombogenic selectin proteins. It is thus possible to reduce and eliminate the pathogenic effect of significant thrombogenic factors. The NHE inhibitors of the present invention can therefore be combined with other anticoagulant and/or thrombolytic active ingredients such as, for example, recombinant or natural tissue plasminogen activator, streptokinase, urokinase, acetylsalicylic acid, thrombin antagonists, factor Xa antagonists, medicinal substances with fibrinolytic activity, thromboxane receptor antagonists, phosphodiesterase inhibitors, factor VIIa antagonists, clopidogrel, ticlopidine etc. Combined use of the present NHE inhibitors with NCBE inhibitors and/or with inhibitors of carbonate dehydratase such as, for example, with acetazolamide, is particularly beneficial.

The compounds of the formula I and/or the pharmaceutically acceptable salts thereof used according to the invention are additionally distinguished by a strong inhibitory effect on the proliferation of cells, for example fibroblast proliferation and the proliferation of smooth vascular muscle cells. The compounds of the formula I and/or the pharmaceutically acceptable salts thereof are therefore suitable as valuable therapeutic agents for diseases in which cellular proliferation represents a primary or secondary cause, and can therefore be used as antiatherosclerotics, agents for chronic renal failure, cancers.

It was possible to show that cell migration is inhibited by NHE inhibitors. The compounds of the formula I and/or the pharmaceutically acceptable salts thereof are therefore suitable as valuable therapeutic agents for diseases in which cell migration represents a primary or secondary cause, such as, for example, cancers with a pronounced tendency to metastasis.

The compounds of the formula I and/or the pharmaceutically acceptable salts thereof are further distinguished by a retardation or prevention of fibrotic disorders. They are thus suitable as excellent agents for the treatment of cardiac fibroses, and of pulmonary fibrosis, hepatic fibrosis, renal fibrosis and other fibrotic disorders.

They can thus be used for the treatment of organ hypertrophies and hyperplasias, for example of the heart and the prostate. They are therefore suitable for the prevention and treatment of heart failure (congestive heart failure=CHF) and for the treatment and prevention of prostate hyperplasia or prostate hypertrophy.

Since there is significant elevation in NHE in essential hypertensives, the compounds of the formula I and/or the pharmaceutically acceptable salts thereof are suitable for the prevention and treatment of high blood pressure and of cardiovascular disorders. In these cases they can be used alone or with a suitable combination and formulation partner for the treatment of high blood pressure and of cardiovascular disorders. Thus, for example, they can be combined with one or more diuretics with a thiazide-like action, loop diuretics, aldosterone and pseudoaldosterone antagonists, such as hydrochlorothiazide, indapamide, polythiazide, furosemide, piretanide, torasemide, bumetanide, amiloride, triamterene, spironolactone or eplerone. The NHE inhibitors of the present invention can further be used in combination with calcium channel blockers such as verapamil, diltiazem, amlodipine or nifedipine, and with ACE inhibitors such as, for example, ramipril, enalapril, lisinopril, fosinopril or captopril. Further beneficial combination partners are also beta-blockers such as metoprolol, albuterol etc., antagonists of the angiotensin receptor and its receptor subtypes such as losartan, irbesartan, valsartan; omapatrilat, gemopatrilat, endothelin antagonists, renin inhibitors, adenosine receptor agonists, inhibitors and activators of potassium channels such as glibenclamide, glimepiride, diazoxide, cromakalim, minoxidil and derivatives thereof, activators of the mitochondrial ATP-sensitive potassium channel (mitoK(ATP) channel), inhibitors of Kv1.5 etc.

It has emerged that NHE1 inhibitors of the formula I and/or the pharmaceutically acceptable salts thereof have a significant antiinflammatory effect and can thus be used as antiinflammatory drugs. Inhibition of the release of mediators of inflammation is noteworthy in this connection. The compounds can thus be used alone or in combination with an antiinflammatory drug for the prevention or treatment of chronic and acute inflammatory disorders. Combination partners advantageously used are steroidal and non-steroidal antiinflammatory drugs. The compounds of the invention can also be used for the treatment of disorders caused by protozoa, of malaria and of coccidiosis in poultry.

It has additionally been found that compounds of the formula I and/or the pharmaceutically acceptable salts thereof show a beneficial effect on serum lipoproteins. It is generally acknowledged that blood fat levels which are too high, called hyperlipoproteinemias, represent an essential risk factor for the development of arteriosclerotic vascular lesions, especially coronary heart disease. The reduction of elevated serum lipoproteins therefore has exceptional importance for the prophylaxis and regression of atherosclerotic lesions. Besides the reduction in total serum cholesterol, it is particularly important to reduce the proportion of specific atherogenic lipid fractions of this total cholesterol, in particular of the low density lipoproteins (LDL) and of the very low density lipoproteins (VLDL), because these lipid fractions represent an atherogenic risk factor. By contrast, a protective function against coronary heart disease is ascribed to the high density lipoproteins. Accordingly, hypolipidemics should be able to reduce not only total cholesterol but, in particular, the VLDL and LDL serum cholesterol fractions. It has now been found that NHE1 inhibitors show valuable therapeutically utilizable properties in relation to influencing the serum lipid levels. Thus, they significantly reduce the elevated serum concentrations of LDL and VLDL as are to be observed, for example, due to increased dietary intake of a cholesterol- and lipid-rich diet or in cases of pathological metabolic alterations, for example genetically related hyperlipidemias. They can therefore be used for the prophylaxis and regression of atherosclerotic lesions by eliminating a causal risk factor. Included herein are not only the primary hyperlipidemias but also certain secondary hyperlipidemias occurring, for example, in association with diabetes. In addition, the compounds of the formula I and/or the pharmaceutically acceptable salts thereof lead to a marked reduction in the infarctions induced by metabolic abnormalities and, in particular, to a significant reduction in the induced infarct size and the severity thereof. Said compounds are therefore advantageously used for producing a medicament for the treatment of hypercholesterolemia; for producing a medicament for the prevention of atherogenesis; for producing a medicament for the prevention and treatment of atherosclerosis, for producing a medicament for the prevention and treatment of diseases induced by elevated cholesterol levels, for producing a medicament for the prevention and treatment of diseases induced by endothelial dysfunction, for producing a medicament for the prevention and treatment of atherosclerosis-induced hypertension, for producing a medicament for the prevention and treatment of atherosclerosis-induced thromboses, for producing a medicament for the prevention and treatment of hypercholesterolemia-induced and endothelial dysfunction-induced ischemic damage and post-ischemic reperfusion damage, for producing a medicament for the prevention and treatment of hypercholesterolemia-induced and endothelial dysfunction-induced cardiac hypertrophies and cardiomyopathies and of congestive heart failure (CHF), for producing a medicament for the prevention and treatment of hypercholesterolemia-induced and endothelial dysfunction-induced coronary vasospasms and myocardial infarctions, for producing a medicament for the treatment of said disorders in combinations with hypotensive substances, preferably with angiotensin converting enzyme (ACE) inhibitors and angiotensin receptor antagonists. A combination of an NHE inhibitor of the formula I and/or the pharmaceutically acceptable salts thereof with an active ingredient lowering the blood fat levels, preferably with an HMG-CoA reductase inhibitor (for example lovastatin or pravastatin), the latter bringing about a hypolipidemic effect and thus increasing the hypolipidemic properties of the NHE inhibitor of the formula I and/or the pharmaceutically acceptable salts thereof, proves to be a favorable combination with enhanced effect and reduced use of active ingredients.

Thus, compounds of the formula I and/or the pharmaceutically acceptable salts thereof lead to effective protection against endothelial damage of various origins. This protection of the vessels against the syndrome of endothelial dysfunction means that the compounds of the formula I and/or the pharmaceutically acceptable salts thereof are valuable medicaments for the prevention and treatment of coronary vasospasms, peripheral vascular diseases, in particular intermittent claudication, atherogenesis and atherosclerosis, left ventricular hypertrophy and dilated cardiomyopathy and thrombotic disorders.

It has additionally been found that compounds of the formula I and/or the pharmaceutically acceptable salts thereof are suitable in the treatment of non-insulin-dependent diabetes (NIDDM), with the insulin resistance being restrained. It may in this connection be beneficial, to enhance the antidiabetic activity and quality of the effect of the compounds of the invention, to combine them with a biguanide such as metformin, with an antidiabetic sulfonylurea such as glyburide, glimepiride, tolbutamide etc., with a glucosidase inhibitor, with a PPAR agonist such as rosiglitazone, pioglitazone etc., with an insulin product of different administration form, with a DB4 inhibitor, with an insulin sensitizer or with meglitinide.

Besides the acute antidiabetic effects, the compounds of the formula I and/or the pharmaceutically acceptable salts thereof counteract the development of late complications of diabetes and can therefore be used as medicaments for the prevention and treatment of late damage from diabetes, such as diabetic nephropathy, diabetic retinopathy, diabetic cardiomyopathy and other disorders occurring as a consequence of diabetes. They can in this connection be advantageously combined with the antidiabetic medicaments just described under NIDDM treatment. The combination with a beneficial dosage form of insulin should be particularly important in this connection.

The NHE inhibitors of the invention of the formula I and/or the pharmaceutically acceptable salts thereof show, besides the protective effects against acute ischemic events and the subsequent equally acutely stressing reperfusion events, also direct therapeutically utilizable effects against diseases and disorders of the entire mammalian organism which are associated with the manifestations of the chronically progressive aging process and which occur independently of acute hypoperfusion states and under normal, non-ischemic conditions. These pathological, age-related manifestations induced over the long aging period, such as illness, invalidity and death, which can now be made amenable to treatment with NHE inhibitors, are diseases and disorders which are essentially caused by age-related changes in vital organs and the function thereof and become increasingly important in the aging organism.

Disorders connected with an age-related functional impairment or with age-related manifestations of wear of organs are, for example, the inadequate response and reactivity of the blood vessels to contraction and relaxation reactions. This age-related decline in the reactivity of vessels to constricting and relaxing stimuli, which are an essential process of the cardiovascular system and thus of life and health, can be significantly eliminated or reduced by NHE inhibitors. One important function and a measure of the maintenance of the reactivity of vessels is the blockade or retardation of the age-related progression in endothelial dysfunction, which can be eliminated highly significantly by NHE inhibitors. The compounds of the formula I and/or the pharmaceutically acceptable salts thereof are thus outstandingly suitable for the treatment and prevention of the age-related progression in endothelial dysfunction, especially of intermittent claudication.

An example of another variable characterizing the aging process is the decline in the contractability of the heart and the decline in the adaptation of the heart to a required pumping output of the heart. This diminished efficiency of the heart as a consequence of the aging process is in most cases connected with a dysfunction of the heart which is caused inter alia by deposition of connective tissue in the myocardial tissue. This deposition of connective tissue is characterized by an increase in the weight of the heart, by an enlargement of the heart and by restrictive cardiac function. It was surprising that it was possible almost completely to inhibit such aging of the heart organ. The compounds of the formula I and/or the pharmaceutically acceptable salts thereof are thus outstandingly suitable for the treatment and prevention of heart failure, of congestive heart failure (CHF).

Whereas preceding patents and patent applications have claimed the treatment of various forms of cancer which have already occurred, it was now extremely surprising that not only is it possible to cure a cancer which has already occurred through inhibition of proliferation, but there is also prevention and highly significant retardation of the age-related incidence of cancer through NHE inhibitors. A particularly noteworthy finding is that the disorders, occurring as a result of aging, of all organs and not only certain types of cancer are suppressed or occur with a highly significant delay. The compounds of the formula I and/or the pharmaceutically acceptable salts thereof are thus outstandingly suitable for the treatment and, in particular, the prevention of age-related types of cancer.

There is now found to be not only a delay, shifted highly significantly in time and beyond the normal statistical extent, in the occurrence of age-related disorders of all the organs investigated, including the heart, vessels, liver etc., and a highly significant delay in cancer of the elderly. On the contrary, there is also surprisingly a prolongation of life to an extent which has to date been achievable by no other group of medicaments or by any natural products. This unique effect of NHE inhibitors also makes it possible, besides the use of the active ingredients alone on humans and animals, to combine these NHE inhibitors with other active principles, measures, substances and natural products which are used in gerontology and which are based on a different mechanism of action. Such classes of active ingredients used in gerontological therapy are: in particular vitamins and substances with antioxidant activity. Since there is a correlation between caloric load or food intake and the aging process, the combination with dietary measures can take place for example with appetite suppressants. It is likewise possible to consider a combination with hypotensive medicaments such as with ACE inhibitors, angiotensin receptor antagonists, diuretics, $Ca^{2+}$ antagonists etc. or with metabolism-normalizing medicaments such as cholesterol-lowering agents.

The compounds of the formula I and/or the pharmaceutically acceptable salts thereof are thus outstandingly suitable for the prevention of age-related tissue changes and for prolonging life while retaining a high quality of life.

The compounds of the invention are effective inhibitors of the cellular sodium-proton antiporter (Na/H exchanger) which in a large number of disorders (essential hypertension, atherosclerosis, diabetes etc.) is also increased in cells which are readily amenable to measurements, such as, for example, in erythrocytes, platelets or leucocytes. The compounds according to the invention are therefore suitable as outstanding and simple scientific tools, for example in their use as diagnostic agents for determining and distinguishing different types of hypertension, but also of atherosclerosis, diabetes and the late complications of diabetes, proliferative disorders etc.

The present invention also relates to processes for synthesising 3-guanidinocarbonyl-1-heteroaryl-indole derivatives of the formula (I)

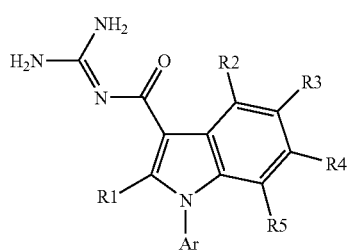

The compounds of the formula (I) can be prepared from a 3-alkoxycarbonyl-1H-indoles of the formula (II) in accordance with the following general synthetic scheme:

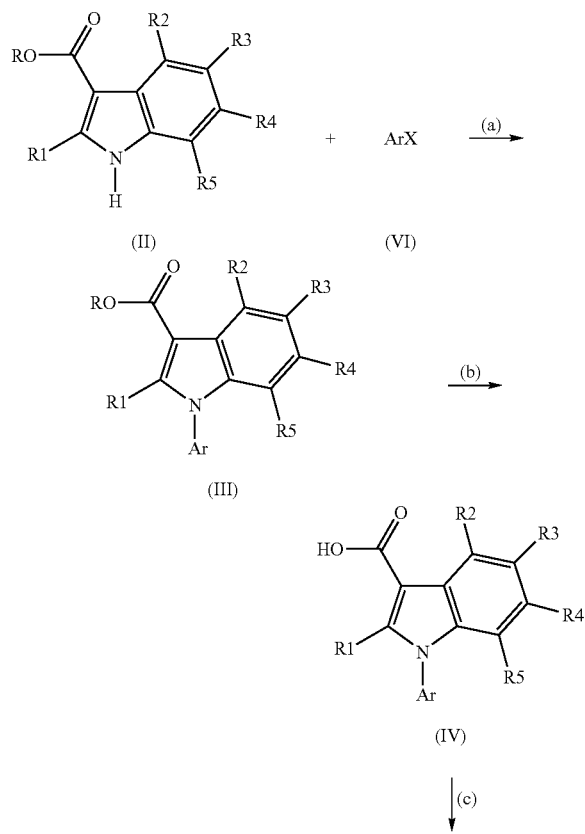

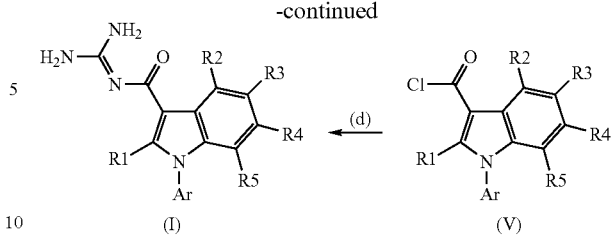

The general synthetic scheme is as follows:
a) a heteroaryl halide ArX of the formula (VI) is reacted with a 3-alkoxycarbonyl-1H-indole of the formula (II)
b) the obtained 3-alkoxycarbonyl-1-heteroaryl-indole of the formula (III) is saponified
c) the 3-carboxy-1-heteroaryl-indole of the formula (IV) is converted in the acid chloride of formula (V)
d) the obtained product of formula (V) is reacted with guanidine wherein in the compounds of the formula II, III, IV, V and VI Ar and R1 to R5 are defined as in the compounds of the formula I,
X is F, Cl, Br or I and
R is alkyl having 1, 2, 3, 4, 5 or 6 carbon atoms.

The product is isolated and is optionally converted into a pharmaceutically acceptable salt.

The compounds of the formula (II) that are not commercially available can be obtained by application or adaptation of methods described in the literature, for example by Toyota M. et al., J. Chem. Soc. Perkin Trans. 1 (1992), (5), 547-52 and in WO 00/71537, the content of which is incorporated herein by reference.

Reaction (a) between a suitable 3-alkoxycarbonyl-1H-indole of the formula (II) and a suitable heteroaryl halide ArX of the formula (VI) is preferably performed under an inert atmosphere (for example under nitrogen or under argon) in a basic medium, for example in the presence of potassium carbonate in an inert solvent, such as dimethyl sulphoxide, at a temperature of between 20° C. and the boiling point of the reaction, medium, preferably at a temperature in the region of 100° C., or in the presence of sodium hydride in an inert solvent, such as dimethylformamide, at a temperature of between 20° C. and the boiling point of the reaction medium, preferably at a temperature in the region of 120° C.

Alternatively, the reaction (a) between a suitable 3-alkoxycarbonyl-1H-indole of the formula (II) and a suitable heteroaryl halide ArX of the formula (VI) can preferably be performed under an inert atmosphere (for example under nitrogen or under argon) in a basic medium, for example in the presence of potassium orthophosphate, copper iodide and trans-1,2-cyclohexanediamine, in an inert solvent, such as a mixture of 1,4-dioxane and of n-dodecane, at a temperature of between 20° C. and the boiling point of the reaction medium, preferably at a temperature in the region of 100° C.

Reaction (b) is generally performed according to the usual methods which do not affect the rest of the molecule, especially by applying the methods described by T. W. Greene and P. G. M. Wuts, Protective Groups in Organic Synthesis (2nd ed.), A. Wiley, Interscience Publication (1991), or by McOmie, Protective Groups in Organic Chemistry, Plenum Press (1973), or by Bradford P. Mundy and Michael G. Ellerd, Name Reactions and Reagents in Organic Synthesis, A. Wiley, Interscience Publication (1988), the content of each of which is incorporated herein by reference. For example, the saponification reaction (b) of a suitable 3-alkoxycarbonyl-1- heteroaryl-1H-indole of the formula (III) is performed in a basic medium, for example in the presence of lithium hydroxide monohydrate, in an inert solvent, such as a mixture of tetrahydrofuran and water, at a temperature of between 20° C. and the boiling point of the reaction medium, preferably at the reflux point of the reaction medium.

Reaction (c) is generally performed according to the usual methods which do not affect the rest of the molecule, especially by applying the methods described by Bradford P. Mundy and Michael G. Ellerd, Name Reactions and Reagents in Organic Synthesis, A. Wiley, Interscience Publication (1988), the content of which is incorporated by reference. For example, the reaction (c) for the formation of the acid chloride of a suitable 3-carboxy-1-heteroaryl-1H-indole of the formula (IV) is preferably performed under an inert atmosphere (for example under nitrogen or under argon) in the presence of oxalyl chloride in an inert solvent, such as dichloromethane, at a temperature of between 20° C. and the boiling point of the reaction medium, preferably at a temperature in the region of 20° C., or in the presence of sulphinyl chloride in an inert solvent, such as chloroform, at a temperature of between 20° C. and the boiling point of the reaction medium, preferably at the reflux point of the reaction medium.

Reaction (d) between a suitable 3-chlorocarbonyl-1-heteroaryl-1H-indole of the formula (V) and guanidine is preferably performed under an inert atmosphere (for example under nitrogen or under argon) in an inert solvent, such as 1,2-dimethoxyethane or tetrahydrofuran, at a temperature in the region of 20° C.

The compounds of the formula (I) are isolated and can be purified by the usual known methods, for example by crystallisation, chromatography or extraction.

The compounds of the formula I can optionally be converted into addition salts with an inorganic or organic acid by reacting with such an acid in a solvent, e.g. an organic solvent such as an alcohol, a ketone, an ether or a chlorinated solvent. These salts also form part of the invention. Examples of pharmaceutically acceptable salts that can be mentioned include the following salts: benzenesulphonate, hydrobromide, hydrochloride, acetate, citrate, ethanesulphonate, fumarate, gluconate, iodate, maleate, isethionate, methanesulphonate, methylenebis(β-oxynaphthoate), nitrate, oxalate, pamoate, phosphate, salicylate, succinate, sulphate, tartrate, theophyllinacetate and p-toluenesulphonate.

If the compounds contain an acid group, they are capable of forming salts with bases, for example alkali metal salts, preferably sodium or potassium salts, or ammonium salts, for example salts with ammonia or organic amines or amino acids. They can also be present as zwitterions.

The examples that follow illustrate the invention.

EXAMPLE 1 a) 3-Guanidinocarbonyl-1-(isoquinol-1-yl)-1H-indole hydrochloride

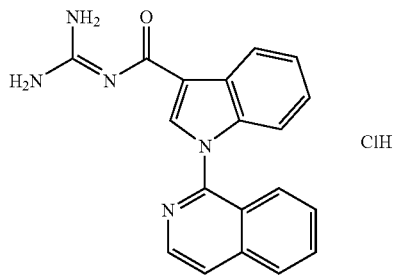

0.483 g (21 mmol) of sodium is added at 25° C. under an argon atmosphere to 60 cm³ of methanol. After complete dissolution, 1.9 g (20 mmol) of guanidine hydrochloride are added. After stirring for 2 hours at 25° C., the reaction mixture is filtered under an argon atmosphere. The filtrate is concentrated to dryness under reduced pressure (2.7 kPa) to give a residue which is dissolved in 30 cm³ of 1,2-dimethoxyethane. 1.2 g of 3-chlorocarbonyl-1-(isoquinol-1-yl)-1H-indole hydrochloride, suspended in 30 cm³ of 1,2-dimethoxyethane, are then added at 25° C. under an argon atmosphere. After stirring at 25° C. for 48 hours, the reaction mixture is concentrated to dryness under reduced pressure (2.7 kPa) to give a residue which is triturated in 25 cm³ of water and 1 cm³ of aqueous 1N hydrochloric acid solution for 1 hour. After filtering off and drying the solid residue under reduced pressure (2.7 kPa) at 40° C., 1.5 g of a pinkish solid are obtained, which solid is purified by flash chromatography [eluent: cyclohexane/ethyl acetate (5/5 and 3/7 by volume) and then dichloromethane/methanol/20% aqueous ammonia (12/3/0.5 by volume)]. After concentrating the fractions under reduced pressure, 1.2 g of a beige-coloured solid are obtained, which solid is triturated in 12 cm³ of N hydrochloric acid for 1 hour. After filtering, the filtrate is concentrated to dryness under reduced pressure (2.7 kPa) to give a residue which is recrystallised under hot conditions from 195 cm³ of methanol to give 0.535 g of 3-guanidinocarbonyl-1-(isoquinol-1-yl)-1H-indole hydrochloride in the form of beige-coloured crystals melting at 262° C. (analysis $C_{19}H_{15}N_5O \cdot HCl$; % calculated C: 62.38; H: 4.41, Cl: 9.69, N: 19.14, O: 4.37; %. Found C: 62.56, H: 4.39, Cl: 9.53, N: 19.19).

b) 3-Chlorocarbonyl-1-(isoquinol-1-yl)-1H-indole hydrochloride 35 cm³ of thionyl chloride are added at 25° C. under an argon atmosphere to 1.2 g (4 mmol) of 3-carboxy-1-(isoquinol-1-yl)-1H-indole. After stirring at reflux for 4 hours, the reaction mixture is concentrated to dryness under reduced pressure (2.7 kPa), successively triturated twice with 10 cm³ of dimethoxyethane and then concentrated to dryness under reduced pressure (2.7 kPa) to give 1.3 g of 3-chlorocarbonyl-1-(isoquinol-1-yl)-1H-indole hydrochloride in the form of a pale yellow solid which is used directly in the following step.

c) 3-Carboxy-1-(isoquinol-1-yl)-1H-indole 0.333 g (7.94 mmol) of lithium hydroxide monohydrate and 60 cm³ of water are added at 25° C. to 1.2 g (3.97 mmol) of 3-methoxycarbonyl-1-(isoquinol-1-yl)-1H-indole dissolved in 60 cm³ of tetrahydrofuran. After stirring at reflux for 22 hours, the reaction mixture is concentrated to dryness under reduced pressure (2.7 kPa) to give a residue which is taken up in 30 cm³ of water and then triturated with 8 cm³ of 5N hydrochloric acid. After filtering off and drying the solid residue under reduced pressure (2.7 kPa) at 40° C., 1.2 g of 3-carboxy-1-(isoquinol-1-yl)-1H-indole are obtained in the form of a white solid. Mass spectrum (EI): m/e 288 (M⁺·), m/e 243.

d) 3-Methoxycarbonyl-1-(isoquinol-1-yl)-1H-indole 1.73 g (12.5 mmol) of potassium carbonate are added at 20° C. under an argon atmosphere to 0.876 g (5 mmol) of 3-methoxycarbonyl-1H-indole in 10 cm³ of dimethyl sulphoxide. After stirring at 20° C. for 1 hour, 0.818 g (5 mmol) of 1-chloroisoquinoline is added. After stirring at 100° C. for 19 hours, the reaction mixture is cooled and diluted with 20 cm³ of ethyl acetate and then washed with 3 times 20 cm³ of water and 20 cm³ of saturated aqueous sodium chloride solution. After separating the phases by settling, the organic phase is dried over anhydrous magnesium sulphate, filtered and concentrated to dryness under reduced pressure (2.7 kPa) to give 1.35 g of 3-methoxycarbonyl-1-(isoquinol-1-yl)-1H-indole in the form of a white solid melting at 140° C.

EXAMPLE 2 a) 3-Guanidinocarbonyl-1-(quinol-4-yl)-1H-indole hydrochloride

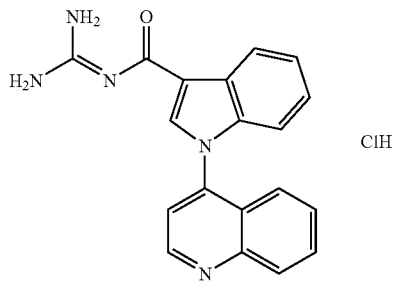

0.32 g (13.8 mmol) of sodium is added at 22° C. under an argon atmosphere to 40 cm³ of methanol. After complete dissolution, 1.25 g (13.1 mmol) of guanidine hydrochloride are added. After stirring at 22° C. for 2 hours, the reaction mixture is filtered under an argon atmosphere. The filtrate is concentrated to dryness under reduced pressure (2.7 kPa) to give a residue which is dissolved in 20 cm³ of 1,2-dimethoxyethane. 1.2 g of 3-chlorocarbonyl-1-(quinol-4-yl)-1H-indole hydrochloride, suspended in 20 cm³ of 1,2-dimethoxyethane, are subsequently added at 22° C. under an argon atmosphere. After stirring at 22° C. for 18 hours, the reaction mixture is concentrated to dryness under reduced pressure (2.7 kPa) to give a residue which is triturated in 20 cm³ of water. After stirring at 22° C. for 1 hour, a few drops of aqueous 10N hydrochloric acid solution are added to neutrality. After filtering off and drying the solid residue under reduced pressure (2.7 kPa) at 40° C., 1.6 g of a beige-coloured solid are obtained, which solid is purified by flash chromatography [eluent: cyclohexane/ethyl acetate (3/7 by volume) and then dichloromethane/methanol/20% aqueous ammonia (12/3/0.5 and 12/4.5/0.75 by volume)]. After concentrating the fractions under reduced pressure, 0.7 g of a beige-coloured foam is obtained, which foam is triturated in 10 cm³ of N hydrochloric acid for 1 hour. After filtering off, the residue is recrystallised under hot conditions from 100 cm³ of methanol to give 0.475 g of 3-guanidinocarbonyl-1-(quinol-4-yl)-1H-indole hydrochloride in the form of pale yellow crystals melting at 270° C. IR spectrum (KBr): 3381, 1694, 1593, 1537, 1508, 1205 and 767 cm⁻¹.

b) 3-Chlorocarbonyl-1-(quinol-4-yl)-1H-indole hydrochloride 25 cm³ of thionyl chloride are added at 25° C. under an argon atmosphere to 0.85 g (2.6 mmol) of 3-carboxy-1-(quinol-4-yl)-1H-indole. After stirring at reflux for 3 hours, the reaction mixture is concentrated to dryness under reduced pressure (2.7 kPa), successively triturated twice with 10 cm³ of dimethoxyethane and then concentrated to dryness under reduced pressure (2.7 kPa) to give 0.9 g of 3-chlorocarbonyl-1-(quinol-4-yl)-1H-indole hydrochloride in the form of a yellow solid which is used directly in the following step.

c) 3-Carboxy-1-(quinol-4-yl)-1H-indole 0.37 g (8.84 mmol) of lithium hydroxide monohydrate and 45 cm³ of water are added at 25° C. to 0.89 g (2.95 mmol) of 3-methoxycarbonyl-1-(quinol-4-yl)-1H-indole dissolved in 45 cm³ of tetrahydrofuran. After stirring at reflux for 17 hours, the reaction mixture is concentrated to dryness under reduced pressure (2.7 kPa) to give a residue which is taken up in 30 cm³ of water and then triturated with 8.8 cm³ of N hydrochloric acid. After filtering off and drying the solid residue under reduced pressure (2.7 kPa) at 40° C., 1 g of 3-carboxy-1-(quinol-4-yl)-1H-indole is obtained in the form of a yellow solid. Mass spectrum (EI): m/e 288 (M⁺·), m/e 243.

d) 3-Methoxycarbonyl-1-(quinol-4-yl)-1H-indole 1.73 g (12.5 mmol) of potassium carbonate are added at 20° C. under an argon atmosphere to 0.876 g (5 mmol) of 3-methoxycarbonyl-1H-indole in 10 cm³ of dimethyl sulphoxide. After stirring at 20° C. for 1 hour, 0.654 cm³ (5 mmol) of 4-chloroquinoline is added. After stirring at 100° C. for 43 hours, the reaction mixture is cooled and diluted with 20 cm³ of ethyl acetate and then washed with 3 times 10 cm³ of water and 10 cm³ of saturated aqueous sodium chloride solution. After separating the phases by settling, the organic phase is dried over anhydrous magnesium sulphate, filtered and concentrated to dryness under reduced pressure (2.7 kPa) to give 2.30 g of a residue which is purified by flash chromatography [eluent: cyclohexane/ethyl acetate (7/3 by volume)]. After concentrating the fractions under reduced pressure, 1.07 g of 3-methoxycarbonyl-1-(quinol-4-yl)-1H-indole are obtained in the form of a white solid melting at 142° C.

EXAMPLE 3 a) 3-Guanidinocarbonyl-1-(quinol-2-yl)-1H-indole hydrochloride

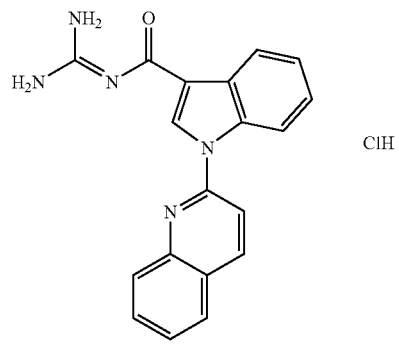

0.35 g (15.2 mmol) of sodium is added at 22° C. under an argon atmosphere to 45 cm³ of methanol. After complete dissolution, 1.36 g (14.32 mmol) of guanidine hydrochloride are added. After stirring at 22° C. for 2 hours, the reaction mixture is filtered under an argon atmosphere. The filtrate is concentrated to dryness under reduced pressure (2.7 kPa) to give a residue which is dissolved in 25 cm³ of 1,2-dimethoxyethane. 0.9 g of 3-chlorocarbonyl-1-(quinol-2-yl)-1H-indole hydrochloride, suspended in 25 cm³ of 1,2-dimethoxyethane, is subsequently added at 22° C. under an argon atmosphere. After stirring at 22° C. for 19 hours and after 2 hours at 85° C., the reaction mixture is concentrated to dryness under reduced pressure (2.7 kPa) to give a residue which is triturated in 50 cm³ of water. After stirring at 22° C. for 1 hour, the suspension is filtered and dried to give a beige-coloured solid which is purified by flash chromatography [eluent: cyclohexane/ethyl acetate (5/5 by volume) and then dichloromethane/methanol/ 20% aqueous ammonia (12/3/0.5 by volume)]. After concentrating the fractions under reduced pressure, 0.7 g of a pale yellow foam is obtained, which foam is triturated in 15 cm³ of N hydrochloric acid for 1 hour. After filtering off, the residue is recrystallised under hot conditions from 220 cm³ of methanol to give 0.6 g of 3-guanidinocarbonyl-1-(quinol-2-yl)-1H-indole hydrochloride in the form of white crystals melting at 268° C. IR spectrum (KBr): 3379, 3201, 1687, 1597, 1545, 1449, 1283, 1239, 1206 and 745 cm⁻¹.

b) 3-Chlorocarbonyl-1-(quinol-2-yl)-1H-indole hydrochloride 25 cm³ of thionyl chloride are added at 25° C. under an argon atmosphere to 0.93 g (2.86 mmol) of 3-carboxy-1-(quinol-2-yl)-1H-indole. After stirring at reflux for 3 hours, the reaction mixture is concentrated to dryness under reduced pressure (2.7 kPa), successively triturated twice with 10 cm³ of dimethoxyethane and then concentrated to dryness under reduced pressure (2.7 kPa) to give 1 g of 3-chlorocarbonyl-1-(quinol-2-yl)-1H-indole hydrochloride in the form of a yellow solid which is used directly in the following step.

c) 3-Carboxy-1-(quinol-2-yl)-1H-indole 0.390 g (9.3 mmol) of lithium hydroxide monohydrate and 45 cm³ of water are added at 25° C. to 0.935 g (3.1 mmol) of 3-methoxycarbonyl-1-(quinol-2-yl)-1H-indole dissolved in 45 cm³ of tetrahydrofuran. After stirring at the reflux point of the solvent for 18 hours, the reaction mixture is concentrated to dryness under reduced pressure (2.7 kPa) to give a residue which is taken up in 20 cm³ of water and then triturated with 9.3 cm³ of N hydrochloric acid. After filtering off and drying under reduced pressure (2.7 kPa) at 40° C., 1 g of 3-carboxy-1-(quinol-2-yl)-1H-indole is obtained in the form of a white solid. Mass spectrum (DCI): m/e 289 (M+H)⁺.

d) 3-Methoxycarbonyl-1-(quinol-2-yl)-1H-indole 1.73 g (12.5 mmol) of potassium carbonate are added at 20° C. under an argon atmosphere to 0.876 g (5 mmol) of 3-methoxycarbonyl-1H-indole in 10 cm³ of dimethyl sulphoxide. After stirring at 20° C. for 1 hour, 0.818 g (5 mmol) of 2-chloroquinoline is added. After stirring at 100° C. for 48 hours, the reaction mixture is cooled and diluted with 100 cm³ of ethyl acetate and then washed with 3 times 50 cm³ of water and 25 cm³ of saturated aqueous sodium chloride solution. After separating the phases by settling, the organic phase is dried over anhydrous magnesium sulphate, filtered and concentrated to dryness under reduced pressure (2.7 kPa) to give 1.4 g of a residue which is purified by flash chromatography [eluent: cyclohexane/ethyl acetate (8/2 by volume)]. After concentrating the fractions under reduced pressure, 0.7 g of 3-methoxycarbonyl-1-(quinol-2-yl)-1H-indole is obtained in the form of a white solid melting at 142° C.

EXAMPLE 4 a) 3-Guanidinocarbonyl-1-(isoquinol-1-yl)-5-methyl-1H-indole hydrochloride

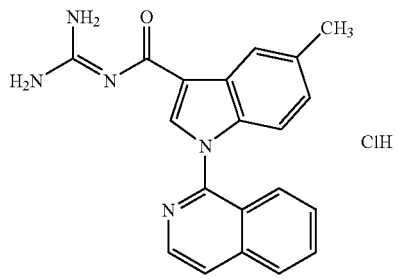

0.457 g (19.8 mmol) of sodium is added at 20° C. under an argon atmosphere to 60 cm³ of methanol. After complete dissolution, 1.79 g (18.75 mmol) of guanidine hydrochloride are added. After stirring at 20° C. for 2 hours, the reaction mixture is filtered under an argon atmosphere. The filtrate is concentrated to dryness under reduced pressure (2.7 kPa) to give a residue which is dissolved in 20 cm³ of 1,2-dimethoxyethane. 1.2 g of 3-chlorocarbonyl-1-(isoquinol-1-yl)-5-methyl-1H-indole hydrochloride, suspended in 40 cm³ of 1,2-dimethoxyethane, are subsequently added at 20° C. under an argon atmosphere. After stirring at 20° C. for 17.5 hours, the reaction mixture is concentrated to dryness under reduced pressure (2.7 kPa) to give a residue which is triturated in 20 cm³ of water. After stirring at 22° C. for 1 hour, the suspension is filtered and then dried to give a beige-coloured solid which is purified by flash chromatography [eluent: cyclohexane/ethyl acetate (7/3 by volume) and then dichloromethane/methanol/20% aqueous ammonia (18/3/0.5 by volume)]. After concentrating the fractions under reduced pressure, 1.2 g of a beige-coloured solid are obtained, which solid is triturated in 12 cm³ of N hydrochloric acid for 1 hour. After filtering off, the residue is recrystallised under hot conditions from 80 cm³ of methanol to give 0.885 g of 3-guanidinocarbonyl-1-(isoquinol-1-yl)-5-methyl-1H-indole hydrochloride in the form of beige-coloured crystals melting at 268° C. IR spectrum (KBr): 3350, 3092, 1693, 1625, 1524, 1462, 1406, 1216 and 832 cm⁻¹.

b) 3-Chlorocarbonyl-1-(isoquinol-1-yl)-5-methyl-1H-indole hydrochloride 15 cm³ of thionyl chloride are added at 20° C. under an argon atmosphere to 1.27 g (3.75 mmol) of 3-carboxy-1-(isoquinol-1-yl)-5-methyl-1H-indole. After stirring at reflux for 4 hours, the reaction mixture is concentrated to dryness under reduced pressure (2.7 kPa), successively triturated twice with 10 cm³ of dimethoxyethane and then concentrated to dryness under reduced pressure (2.7 kPa) to give 1.2 g of 3-chlorocarbonyl-1-(isoquinol-1-yl)-5-methyl-1H-indole hydrochloride in the form of a yellow solid which is used directly in the following step.

c) 3-Carboxy-1-(isoquinol-1-yl)-5-methyl-1H-indole 0.319 g (7.59 mmol) of lithium hydroxide monohydrate and 60 cm³ of water are added at 25° C. to 1.2 g (3.79 mmol) of 3-methoxycarbonyl-1-(isoquinol-1-yl)-5-methyl-1H-indole dissolved in 60 cm³ of tetrahydrofuran. After stirring at the reflux point of the solvent for 24 hours, the reaction mixture is concentrated to dryness under reduced pressure (2.7 kPa) to give a residue which is taken up in 30 cm³ of water and then triturated with 11.4 cm³ of N hydrochloric acid. After filtering off and drying the solid residue under reduced pressure (2.7 kPa) at 40° C., 1 g of 3-carboxy-1-(isoquinol-1-yl)-5-methyl-1H-indole is obtained in the form of a white solid. Mass spectrum (EI): m/e 302 (M⁺·), m/e 257.

d) 3-Methoxycarbonyl-1-(isoquinol-1-yl)-5-methyl-1H-indole 1.65 g (11.9 mmol) of potassium carbonate are added at 25° C. under an argon atmosphere to 0.900 g (4.75 mmol) of 3-methoxycarbonyl-5-methyl-1H-indole in 10 cm³ of dimethyl sulphoxide. After stirring at 25° C. for 0.5 hour, 0.677 cm³ (4.75 mmol) of 1-chloroisoquinoline is added. After stirring at 100° C. for 48 hours, the reaction mixture is cooled and diluted with 100 cm³ of ethyl acetate and then washed with 3 times 50 cm³ of water and 25 cm³ of saturated aqueous sodium chloride solution. The organic phase is dried over anhydrous magnesium sulphate, filtered and concentrated to dryness under reduced pressure (2.7 kPa) to give 1.50 g of a residue which is purified by flash chromatography [eluent: cyclohexane/ethyl acetate (8/2 by volume)]. After concentrating the fractions to dryness under reduced pressure (2.7 kPa), 1.4 g of 3-methoxycarbonyl-1-(isoquinol-1-yl)-5-methyl-1H-indole are obtained in the form of a white solid melting at 142° C.

EXAMPLE 5 a) 3-Guanidinocarbonyl-5-methyl-1-(quinol-2-yl)-1H-indole hydrochloride

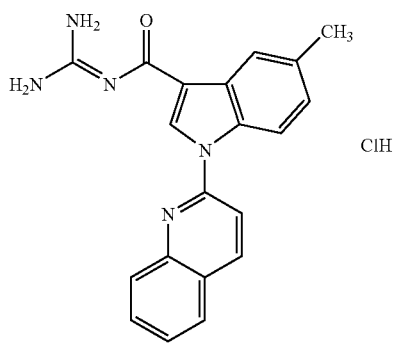

0.328 g (14.3 mmol) of sodium is added at 22° C. under an argon atmosphere to 40 cm³ of methanol. After complete dissolution, 1.28 g (13.5 mmol) of guanidine hydrochloride are added. After stirring at 22° C. for 2 hours, the reaction mixture is filtered under an argon atmosphere. The filtrate is concentrated to dryness under reduced pressure (2.7 kPa) to give a residue which is dissolved in 20 cm³ of 1,2-dimethoxyethane. 1 g of 3-chlorocarbonyl-5-methyl-1-(quinol-2-yl)-1H-indole, suspended in 20 cm³ of 1,2-dimethoxyethane, is subsequently added at 22° C. under an argon atmosphere. After stirring at 22° C. for 19 hours, the reaction mixture is concentrated to dryness under reduced pressure (2.7 kPa) to give a residue which is triturated in 20 cm³ of water. After stirring at 22° C. for 0.5 hour, the suspension is filtered and dried to give a beige-coloured powder which is purified by flash chromatography [eluent: cyclohexane/ethyl acetate (7/3 by volume) and then dichloromethane/methanol/20% aqueous ammonia (18/3/0.5 by volume)]. After concentrating the fractions under reduced pressure, 0.5 g of a yellow foam is obtained, which foam is triturated in 10 cm³ of N hydrochloric acid for 1 hour. After filtering off, the residue is recrystallised under hot conditions from 120 cm³ of methanol to give 0.355 g of 3-guanidinocarbonyl-5-methyl-1-(quinol-2-yl)-1H-indole hydrochloride in the form of white crystals melting at 268° C. (Analysis $C_{20}H_{17}N_5O \cdot HCl$; % calculated C: 63.24, H: 4.78, Cl: 9.33, N: 18.44, O: 4.21, % found C: 63.31, H: 4.88, Cl: 9.26, N: 18.38).

b) 3-Chlorocarbonyl-5-methyl-1-(quinol-2-yl)-1H-indole hydrochloride 15 cm³ of thionyl chloride are added at 22° C. under an argon atmosphere to 0.95 g (2.70 mmol) of 3-carboxy-5-methyl-1-(quinol-2-yl)-1H-indole. After stirring at reflux for 3.5 hours, the reaction mixture is concentrated to dryness under reduced pressure (2.7 kPa), successively triturated twice with 10 cm³ of dimethoxyethane and then concentrated to dryness under reduced pressure (2.7 kPa) to give 1 g of 3-chlorocarbonyl-5-methyl-1-(quinol-2-yl)-1H-indole hydrochloride in the form of a yellow solid which is used directly in the following step.

c) 3-Carboxy-5-methyl-1-(quinol-2-yl)-1H-indole 0.342 g (8.15 mmol) of lithium hydroxide monohydrate and 45 cm³ of water are added at 25° C. to 0.86 g (2.7 mmol) of 3-methoxycarbonyl-5-methyl-1-(quinol-2-yl)-1H-indole dissolved in 45 cm³ of tetrahydrofuran. After stirring at reflux for 19 hours, the reaction mixture is concentrated to dryness under reduced pressure (2.7 kPa) to give a residue which is taken up in 20 cm³ of water and then triturated with 8.2 cm³ of N hydrochloric acid. After filtering off and drying the solid residue under reduced pressure (2.7 kPa) at 40° C., 0.95 g of 3-carboxy-5-methyl-1-(quinol-2-yl)-1H-indole is obtained in the form of a white solid. Mass spectrum (EI): m/e 302 (M⁺·).

d) 3-Methoxycarbonyl-5-methyl-1-(quinol-2-yl)-1H-indole 1.63 g (11.8 mmol) of potassium carbonate are added at 25° C. under an argon atmosphere to 0.895 g (4.73 mmol) of 3-methoxycarbonyl-5-methyl-1H-indole in 10 cm³ of dimethyl sulphoxide. After stirring at 25° C. for 0.5 hour, 0.774 g (4.73 mmol) of 2-chloroquinoline is added. After stirring at 100° C. for 48 hours, the reaction mixture is cooled and diluted with 100 cm³ ethyl acetate and then washed with 3 times 50 cm³ of water and 25 cm³ of saturated aqueous sodium chloride solution. After separating the phases by settling, the organic phase is dried over anhydrous magnesium sulphate, filtered and concentrated to dryness under reduced pressure (2.7 kPa) to give 1.2 g of a residue which is recrystallised under hot conditions from 30 cm³ of cyclohexane and 6 cm³ of ethyl acetate to give 0.8 g of 3-methoxycarbonyl-5-methyl-1-(quinol-2-yl)-1H-indole in the form of a white solid melting at 143° C.

EXAMPLE 6 a) 3-Guanidinocarbonyl-5-methyl-1-(quinol-4-yl)-1H-indole hydrochloride

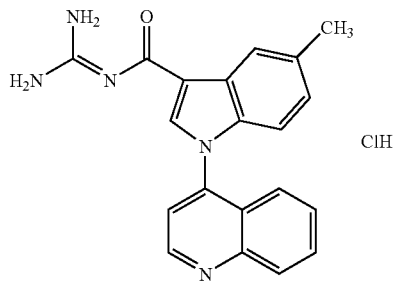

0.365 g (15.9 mmol) of sodium is added at 22° C. under an argon atmosphere to 45 cm³ of methanol. After complete dissolution, 1.4 g (15 mmol) of guanidine hydrochloride are added. After stirring at 22° C. for 2 hours, the reaction mixture is filtered under an argon atmosphere. The filtrate is concentrated to dryness under reduced pressure (2.7 kPa) to give a residue which is dissolved in 25 cm³ of 1,2-dimethoxyethane. 1 g of 3-chlorocarbonyl-5-methyl-1-(quinol-4-yl)-1H-indole, suspended in 20 cm³ of 1,2-dimethoxyethane, is subsequently added at 22° C. under an argon atmosphere. After stirring at 22° C. for 19 hours, the reaction mixture is concentrated to dryness under reduced pressure (2.7 kPa) to give a residue which is triturated in 20 cm³ of water. After stirring at 22° C. for 1 hour, the suspension is filtered and dried to give a beige-coloured powder which is purified by flash chromatography [eluent: cyclohexane/ethyl acetate (7/3 by volume) and then dichloromethane/methanol/20% aqueous ammonia (18/3/0.5 by volume)]. After concentrating the fractions under reduced pressure (2.7 kPa), 1.1 g of a beige-coloured solid are obtained, which solid is triturated in 10 cm³ of N hydrochloric acid for 1 hour. After filtering off, the residue is recrystallised under hot conditions from 180 cm³ of methanol to give 0.66 g of 3-guanidinocarbonyl-5-methyl-1-(quinol-4-yl)-1H-indole hydrochloride in the form of pale yellow crystals melting at 268° C. (Analysis $C_{20}H_{17}N_5O.HCl$; % calculated C, 63.24, H: 4.78, Cl: 9.33, N: 18.44, O: 4.21, % found C: 63.26, H: 4.72, Cl: 9.47, N: 18.57).

b) 3-Chlorocarbonyl-5-methyl-1-(quinol-4-yl)-1H-indole hydrochloride 10 cm³ of thionyl chloride are added at 22° C. under an argon atmosphere to 1 g (3 mmol) of 3-carboxy-5-methyl-1-(quinol-4-yl)-1H-indole. After stirring at reflux for 2.5 hours, the reaction mixture is concentrated to dryness under reduced pressure (2.7 kPa), successively triturated twice with 5 cm³ of dimethoxyethane and then concentrated to dryness under reduced pressure (2.7 kPa) to give 1 g of 3-chlorocarbonyl-5-methyl-1-(quinol-4-yl)-1H-indole hydrochloride in the form of a yellow solid which is used directly in the following step.

c) 3-Carboxy-5-methyl-1-(quinol-4-yl)-1H-indole 0.422 g (10.05 mmol) of lithium hydroxide monohydrate and 50 cm³ of water are added at 25° C. to 1.06 g (3.35 mmol) of 3-methoxycarbonyl-5-methyl-1-(quinol-4-yl)-1H-indole dissolved in 50 cm³ of tetrahydrofuran. After stirring at the reflux point of the solvent for 22 hours, the reaction mixture is concentrated to dryness under reduced pressure (2.7 kPa) to give a residue which is taken up in 25 cm³ of water and then triturated with 10 cm³ of N hydrochloric acid. After filtering off and drying the solid residue under reduced pressure (2.7 kPa) at 40° C., 0.996 g of 3-carboxy-5-methyl-1-(quinol-4-yl)-1H-indole is obtained in the form of a white solid. Mass spectrum (EI): m/e 302 ($M^{+.}$).

d) 3-Methoxycarbonyl-5-methyl-1-(quinol-4-yl)-1H-indole 1.65 g (11.9 mmol) of potassium carbonate are added at 25° C. under an argon atmosphere to 0.9 g (4.75 mmol) of 3-methoxycarbonyl-5-methyl-1H-indole in 10 cm³ of dimethyl sulphoxide. After stirring at 25° C. for 0.5 hour, 0.623 cm³ (4.75 mmol) of 4-chloroquinoline is added. After stirring at 100° C. for 48 hours, the reaction mixture is cooled and diluted with 100 cm³ of ethyl acetate and then washed with 3 times 50 cm³ of water and 25 cm³ of saturated aqueous sodium chloride solution. After separating the phases by settling, the organic phase is dried over anhydrous magnesium sulphate, filtered and concentrated to dryness under reduced pressure (2.7 kPa) to give 1.4 g of a residue which is purified by flash chromatography [eluent: cyclohexane/ethyl acetate (7/3 by volume)]. After concentrating the fractions under reduced pressure, 1.2 g of 3-methoxycarbonyl-5-methyl-1-(quinol-4-yl)-1H-indole are obtained in the form of a white solid melting at 168° C.

EXAMPLE 7 a) 3-Guanidinocarbonyl-1-(quinol-3-yl)-1H-indole hydrochloride

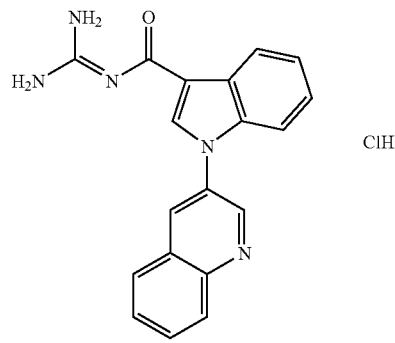

0.282 g (12.25 mmol) of sodium is added at 22° C. under an argon atmosphere to 40 cm³ of methanol. After complete dissolution, 1.1 g (11.5 mmol) of guanidine hydrochloride are added. After stirring at 22° C. for 1.5 hours, the reaction mixture is filtered under an argon atmosphere. The filtrate is concentrated to dryness under reduced pressure (2.7 kPa) to give a residue which is dissolved in 10 cm³ of 1,2-dimethoxyethane. 1 g of 3-chlorocarbonyl-1-(quinol-3-yl)-1H-indole hydrochloride, suspended in 40 cm³ of 1,2-dimethoxyethane, is subsequently added at 22° C. under an argon atmosphere. After stirring at 22° C. for 17.5 hours and after 2 hours at reflux, the reaction mixture is concentrated to dryness under reduced pressure (2.7 kPa) to give a residue which is triturated in 15 cm³ of water. After stirring at 22° C. for 1 hour, the suspension is filtered and dried to give a beige-coloured powder which is purified by flash chromatography [eluent: dichloromethane/methanol/20% aqueous ammonia (12/3/0.5 by volume)]. After concentrating the fractions under reduced pressure, 0.5 g of a beige-coloured foam is obtained, which foam is triturated in 5 cm³ of N hydrochloric acid for 1 hour. After filtering off, the residue is recrystallised under hot conditions from 25 cm³ of methanol to give 0.45 g of 3-guanidinocarbonyl-1-(quinol-3-yl)-1H-indole hydrochloride in the form of white crystals melting at 268° C. Mass spectrum (EI): m/e 329 ($M^{+.}$), m/e 271 (base peak).

b) 3-Chlorocarbonyl-1-(quinol-3-yl)-1H-indole hydrochloride 10 cm³ of thionyl chloride are added at 22° C. under an argon atmosphere to 1 g (2.3 mmol) of 3-carboxy-1-(quinol-3-yl)-1H-indole. After stirring at reflux for 1.5 hours, the reaction mixture is concentrated to dryness under reduced pressure (2.7 kPa), successively triturated twice with 10 cm³ of dimethoxyethane and then concentrated to dryness under reduced pressure (2.7 kPa) to give 1 g of 3-chlorocarbonyl-1-(quinol-3-yl)-1H-indole hydrochloride in the form of an orange-coloured solid which is used directly in the following step.

c) 3-Carboxy-1-(quinol-3-yl)-1H-indole 0.291 g (6.93 mmol) of lithium hydroxide monohydrate and 30 cm³ of water are added at a temperature in the region of 22° C. to 0.7 g (2.31 mmol) of 3-methoxycarbonyl-1-(quinol-3-yl)-1H-indole dissolved in 30 cm³ of tetrahydrofuran. After stirring at the reflux point of the solvent for 18 hours, the reaction mixture is concentrated to dryness under reduced pressure (2.7 kPa) to give a residue which is taken up in 15 cm³ of water and then triturated with 7 cm³ of N hydrochloric acid. After filtering off and drying the solid residue under reduced pressure (2.7 kPa) at 40° C., 1 g of 3-carboxy-1-(quinol-3-yl)-1H-indole is obtained in the form of a pale yellow solid. Mass spectrum (EI): m/e 288 (M+·).

d) 3-Methoxycarbonyl-1-(quinol-3-yl)-1H-indole 5 cm³ of 1,4-dioxane, 230 cm³ of n-dodecane, 1.04 g (5 mmol) of 3-bromoquinoline and 0.6 cm³ (5 mmol) of trans-1,2-cyclohexanediamine are added at 22° C. under an argon atmosphere to 0.876 g (5 mmol) of 3-methoxycarbonyl-1H-indole, 2.23 g (10.51 mmol) of potassium orthophosphate and 0.09 g (0.5 mmol) of copper iodide. After stirring at 100° C. for 31 hours and after 48 hours at 22° C., the reaction mixture is concentrated to dryness under reduced pressure (2.7 kPa). The residue is diluted with 100 cm³ of ethyl acetate and then washed with 3 times 100 cm³ of water and 25 cm³ of saturated aqueous sodium chloride solution. After separating the phases by settling, the organic phase is dried over anhydrous magnesium sulphate, filtered and concentrated to dryness under reduced pressure (2.7 kPa) to give 1.2 g of a residue which is purified by flash chromatography [eluent: cyclohexane/ethyl acetate (8/2 by volume)]. After concentrating the fractions under reduced pressure, 0.9 g of a yellow solid is obtained, which solid is recrystallised under hot conditions from a cyclohexane (6 cm³)/ethyl acetate (a few drops) mixture to give, after filtering off and drying under reduced pressure (2.7 kPa) at 40° C., 0.15 g of 3-methoxycarbonyl-1-(quinol-3-yl)-1H-indole in the form of a white solid melting at 138° C.

EXAMPLE 8 a) 3-Guanidinocarbonyl-1-(quinol-6-yl)-1H-indole hydrochloride

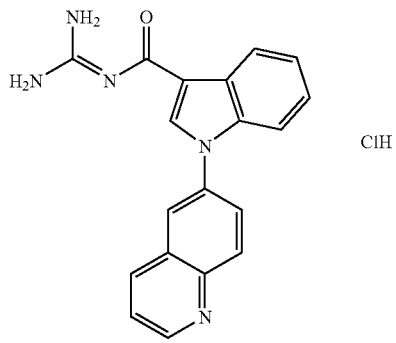

0.256 g (11.1 mmol) of sodium is added at 22° C. under an argon atmosphere to 40 cm³ of methanol. After complete dissolution, 1 g (10.5 mmol) of guanidine hydrochloride is added. After stirring at 22° C. for 3 hours, the reaction mixture is filtered under an argon atmosphere. The filtrate is concentrated to dryness under reduced pressure (2.7 kPa) to give a residue which is dissolved in 10 cm³ of 1,2-dimethoxyethane. 1 g of 3-chlorocarbonyl-1-(quinol-6-yl)-1H-indole hydrochloride, suspended in 40 cm³ of 1,2-dimethoxyethane, is subsequently added at 22° C. under an argon atmosphere. After stirring at 22° C. for 48 hours and after 2 hours at reflux, the reaction mixture is concentrated to dryness under reduced pressure (2.7 kPa) to give a residue which is triturated in 15 cm³ of water. After stirring at 22° C. for 1 hour, a few drops of 10N hydrochloric acid solution are added. After stirring at 22° C. for 12 hours, the suspension is filtered and dried to give 0.52 g of 3-guanidinocarbonyl-1-(quinol-6-yl)-1H-indole hydrochloride in the form of a yellow solid melting at 268° C. IR spectrum (KBr): 3343, 3168, 2174, 1693, 1597, 1543, 1502, 1454, 1236, 1199, 772 and 751 cm⁻¹.

b) 3-Chlorocarbonyl-1-(quinol-6-yl)-1H-indole hydrochloride 20 cm³ of thionyl chloride are added at 22° C. under an argon atmosphere to 0.69 g (2.1 mmol) of 3-carboxy-1-(quinol-6-yl)-1H-indole. After stirring at reflux for 4 hours, the reaction mixture is concentrated to dryness under reduced pressure (2.7 kPa). The residue is successively triturated twice with 10 cm³ of dimethoxyethane and then concentrated to dryness under reduced pressure (2.7 kPa) to give 1 g of 3-chlorocarbonyl-1-(quinol-6-yl)-1H-indole hydrochloride in the form of an orange-coloured solid which is used directly in the following step.

c) 3-Carboxy-1-(quinol-6-yl)-1H-indole 0.283 g (6.75 mmol) of lithium hydroxide monohydrate and 30 cm³ of water are added at 22° C. to 0.68 g (2.25 mmol) of 3-methoxycarbonyl-1-(quinol-6-yl)-1H-indole dissolved in 30 cm³ of tetrahydrofuran. After stirring at the reflux point of the solvent for 31.5 hours, the reaction mixture is concentrated to dryness under reduced pressure (2.7 kPa) to give a residue which is taken up in 15 cm³ of water and then triturated with 6 cm³ of N hydrochloric acid. After filtering off and drying the solid residue under reduced pressure (2.7 kPa) at 40° C., 0.69 g of 3-carboxy-1-(quinol-6-yl)-1H-indole is obtained in the form of a beige-coloured solid. Mass spectrum (DCI): m/e 289 (M+H)⁺, m/e 245.

d) 3-Methoxycarbonyl-1-(quinol-6-yl)-1H-indole 5 cm³ of 1,4-dioxane, 0.230 cm³ of n-dodecane, 1.04 g (5 mmol) of 6-bromoquinoline and 0.6 cm³ (5 mmol) of trans-1,2-cyclohexanediamine are added at 22° C. under an argon atmosphere to 0.876 g (5 mmol) of 3-methoxycarbonyl-1H-indole, 2.23 g (10.51 mmol) of potassium orthophosphate and 0.09 g (0.5 mmol) of copper iodide. After stirring at 100° C. for 26 hours and after 48 hours at 22° C., the reaction mixture is concentrated to dryness under reduced pressure (2.7 kPa). The residue is diluted with 100 cm³ of ethyl acetate and then washed 3 times with 100 cm³ of water and 25 cm³ of saturated aqueous sodium chloride solution. After separating the phases by settling, the organic phase is dried over anhydrous magnesium sulphate, filtered and concentrated to dryness under reduced pressure (2.7 kPa) to give 1.5 g of a residue which is purified by flash chromatography [eluent: cyclohexane/ethyl acetate (6/4 by volume)]. After concentrating the fractions under reduced pressure, 0.8 g of 3-methoxycarbonyl-1-(quinol-6-yl)-1H-indole is obtained in the form of an off-white solid melting at 128° C.

EXAMPLE 9 a) 3-Guanidinocarbonyl-1-(quinol-8-yl)-1H-indole

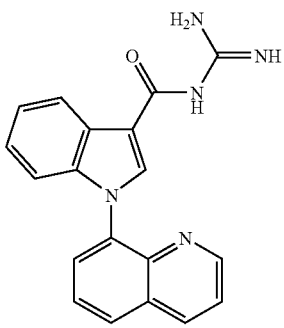

1.25 g (13.09 mmol) of guanidine hydrochloride are added to a solution of 0.71 mg (13.14 mmol) of sodium methoxide in 10 cm³ of methanol at a temperature in the region of 22° C. under an argon atmosphere. After stirring at a temperature in the region of 22° C. for 2 hours, the solvent is evaporated off under reduced pressure (2.7 kPa). The residue, placed under an argon atmosphere, is taken up in 20 cm³ of a tetrahydrofuran/dichloromethane (1/1 by volume) mixture and then 0.9 g (2.62 mmol) of 3-chlorocarbonyl-1-(quinol-8-yl)-1H-indole hydrochloride, dissolved in 5 cm³ of the same tetrahydrofuran/dichloromethane mixture, is added thereto. After 15 hours at a temperature in the region of 22° C. and then heating at a temperature in the region of 60° C. with stirring for 1.5 hours, the reaction mixture is concentrated to dryness under reduced pressure (2.7 kPa) to give a residue which is taken up in dichloromethane. The insoluble material is then filtered off and discarded, and the filtrate is concentrated under reduced pressure (2.7 kPa). The residue obtained is taken up in an ethyl acetate/methanol (8/2 by volume) mixture and the resulting precipitate is filtered off. A white solid is obtained, which solid is crystallised under hot conditions from 10 cm³ of ethanol. The crystals formed are filtered off and dried under vacuum (2.7 kPa) to give 0.51 g of 3-guanidinocarbonyl-1-(quinol-8-yl)-1H-indole in the form of white crystals melting at 172° C. Mass spectrum (EI): m/e 329 (M+·), m/e 271.

b) 3-Chlorocarbonyl-1-(quinol-8-yl)-1H-indole hydrochloride 0.6 cm³ (6.88 mmol) of oxalyl chloride is added to a suspension, cooled to a temperature in the region of 5° C., of 0.74 g (2.28 mmol) of 3-carboxy-1-(quinol-8-yl)-1H-indole hydrochloride in 15 cm³ of dichloromethane under an argon atmosphere. After stirring at a temperature in the region of 22° C. for 15 hours, the reaction mixture is concentrated to dryness under reduced pressure (2.7 kPa) to give 0.9 g of 3-chlorocarbonyl-1-(quinol-8-yl)-1H-indole hydrochloride in the form of a yellow solid which is used directly in the following step.

c) 3-Carboxy-1-(quinol-8-yl)-1H-indole hydrochloride 0.4 g (9.53 mmol) of lithium hydroxide monohydrate and 10 cm³ of water are added to a solution at a temperature in the region of 22° C. of 0.9 g (2.98 mmol) of 3-methoxycarbonyl-1-(quinol-8-yl)-1H-indole in 10 cm³ of tetrahydrofuran. After stirring at the reflux point of the solvent for 15 hours, the reaction mixture is concentrated to dryness under reduced pressure (2.7 kPa) and the residue is taken up in water. The resulting solution is extracted with ethyl acetate and then adjusted to pH 6 with N hydrochloric acid. The solid which appears during acidification is filtered off and dried on a rack, giving 0.74 g of 3-carboxy-1-(quinol-8-yl)-1H-indole hydrochloride in the form of a white solid. Mass spectrum (EI): m/e 288 (M+·), m/e 243.

d) 3-Methoxycarbonyl-1-(quinol-8-yl)-1H-indole 25 cm³ of 1,4-dioxane, 0.256 cm³ of n-dodecane, 1.25 g (4.9 mmol) of 8-iodoquinoline and 0.582 cm³ (4.85 mmol) of trans-1,2-cyclohexanediamine are added at a temperature in the region of 22° C. under an argon atmosphere to 0.850 g (4.85 mmol) of 3-methoxycarbonyl-1H-indole, 2.2 g (10.36 mmol) of potassium orthophosphate and 0.085 g (0.45 mmol) of copper iodide. After stirring at a temperature in the region of 100° C. for 15 hours, the reaction mixture is concentrated to dryness under reduced pressure (2.7 kPa). The residue is diluted with 100 cm³ of ethyl acetate and then washed with twice 100 cm³ of water and 25 cm³ of saturated aqueous sodium chloride solution. After separating the phases by settling, the organic phase is dried over anhydrous magnesium sulphate, filtered and concentrated to dryness under reduced pressure (2.7 kPa) to give 1.2 g of a brown oil which is purified by flash chromatography (eluent: cyclohexane/ethyl acetate (85/15 by volume)]. After concentrating the fractions under reduced pressure, 0.9 g of 3-methoxycarbonyl-1-(quinol-8-yl)-1H-indole is obtained in the form of a yellow oil. IR spectrum (CCl₄): 1711, 1538, 1502, 1198, 1093, 832 and 627 cm⁻¹.

e) 8-iodoquinoline can be prepared according to the method described by M. Howitz et al., Justus Liebigs Ann. Chem. (1913), 396, 63, the content of which is incorporated herein by reference.

EXAMPLE 10 a) 3-Guanidinocarbonyl-1-(isoquinol-3-yl)-1H-indole hydrochloride

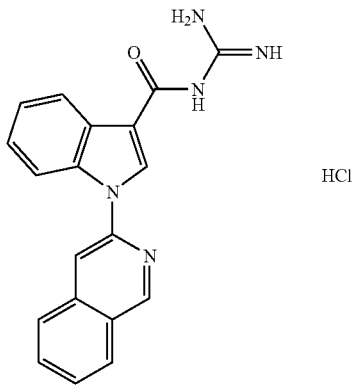

0.974 g (10.2 mmol) of guanidine hydrochloride is added to a solution of 0.55 g (10.2 mmol) of sodium methoxide in 10 cm³ of methanol at a temperature in the region of 22° C. under an argon atmosphere. After stirring at a temperature in the region of 22° C. for 2 hours, the solvent is evaporated off under reduced pressure (2.7 kPa). The residue, placed under an argon atmosphere, is taken up in 20 cm³ of a tetrahydrofuran/dichloromethane (1/1 by volume) mixture and then 0.7 g (2.04 mmol) of 3-chlorocarbonyl-1-(isoquinol-3-yl)-1H-indole hydrochloride, dissolved in 5 cm³ of the same tetrahydrofuran/dichloromethane mixture, is added thereto. After 15 hours at a temperature in the region of 22° C. and then heating at a temperature in the region of 60° C. with stirring for 1 hour, the reaction mixture is concentrated to dryness under reduced pressure (2.7 kPa) to give a residue which is taken up in dichloromethane. The insoluble material is then filtered off and discarded, and the filtrate is concentrated under reduced pressure (2.7 kPa). The residue obtained is purified by flash chromatography [eluent: ethyl acetate/methanol (9/1 by volume)]. After concentrating the fractions under reduced pressure, 0.263 g of 3-guanidinocarbonyl-1-(isoquinol-3-yl)-1H-indole hydrochloride is obtained in the form of a white solid which decomposes at 235° C. Mass spectrum (EI): m/e 329 (M⁺·), m/e 271. IR spectrum (KBr): 3392, 1692, 1629, 1593, 1538, 1514, 1462, 1227, 1202 and 747 cm⁻¹.

b) 3-Chlorocarbonyl-1-(isoquinol-3-yl)-1H-indole hydrochloride 0.7 cm³ (8 mmol) of oxalyl chloride is added to a suspension, cooled to a temperature in the region of 5° C., of 0.74 g (2.57 mmol) of 3-carboxy-1-(isoquinol-3-yl)-1H-indole in 15 cm³ of dichloromethane under an argon atmosphere. After stirring at a temperature in the region of 22° C. for 15 hours, the reaction mixture is concentrated to dryness under reduced pressure (2.7 kPa). The residue, dissolved in 15 cm³ of dichloromethane, is again reacted with 1 cm³ (11.46 mmol) of oxalyl chloride. After stirring at a temperature in the region of 22° C. for 48 hours, the reaction mixture is concentrated to dryness under reduced pressure (2.7 kPa) to give 0.7 g of 3-chlorocarbonyl-1-(isoquinol-3-yl)-1H-indole hydrochloride in the form of a yellow solid which is used directly in the following step.

c) 3-Carboxy-1-(isoquinol-3-yl)-1H-indole 0.5 g (11.92 mmol) of lithium hydroxide monohydrate and 15 cm³ of water are added to a solution at a temperature in the region of 22° C. of 1.1 g (3.64 mmol) of 3-methoxycarbonyl-1-(isoquinol-3-yl)-1H-indole in 15 cm³ of tetrahydrofuran. After stirring at the reflux point of the solvent for 15 hours, the reaction mixture is concentrated to dryness under reduced pressure (2.7 kPa), the residue is triturated in water and the resulting suspension is filtered. The solid obtained is suspended in 20 cm³ of water adjusted to pH 7 with N hydrochloric acid. After stirring at a temperature in the region of 22° C. for 1 hour, the solid is filtered off and dried under reduced pressure (2.7 kPa) to give 0.64 g of 3-carboxy-1-(isoquinol-3-yl)-1H-indole in the form of a white solid. IR spectrum (KBr): 1661, 1629, 1593, 1540, 1464, 1217 and 748 cm⁻¹.

d) 3-Methoxycarbonyl-1-(isoquinol-3-yl)-1H-indole 25 cm³ of 1,4-dioxane, 0.256 cm³ of n-dodecane, 1.25 g (4.9 mmol) of 3-iodoisoquinoline and 0.582 cm³ (4.85 mmol) of trans-1,2-cyclohexanediamine are added at a temperature in the region of 22° C. under an argon atmosphere to 0.850 g (4.85 mmol) of 3-methoxycarbonyl-1H-indole, 2.2 g (10.36 mmol) of potassium orthophosphate and 0.085 g (0.45 mmol) of copper iodide. After stirring at a temperature in the region of 100° C. for 17 hours, the reaction mixture is concentrated to dryness under reduced pressure (2.7 kPa). The residue is diluted with 100 cm³ of dichloromethane, the suspension obtained is filtered and the filtrate is concentrated to dryness under reduced pressure (2.7 kPa) to give 2.3 g of a brown oil which is purified by flash chromatography [eluent: cyclohexane/ethyl acetate (85/15 by volume)]. After concentrating the fractions under reduced pressure, 1.1 g of 3-methoxycarbonyl-1-(isoquinol-3-yl)-1H-indole are obtained in the form of a white solid. Mass spectrum (EI): EI: m/e 302 (M⁺·), m/e 271.

e) 3-iodoisoquinoline can be prepared by the adaptation of the method described by Z. Sui et al., Synth. Commun. (1997), 27, 3581-3590, the content of which is incorporated herein by reference.

EXAMPLE 11 a) 3-Guanidinocarbonyl-6-methoxy-1-(quinol-4-yl)-1H-indole dihydrochloride

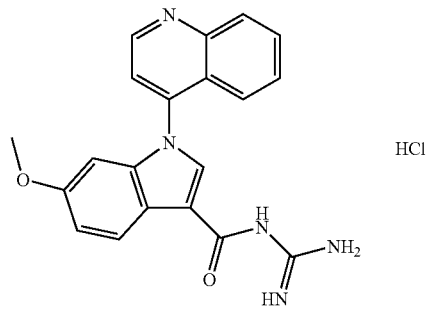

0.87 g (38 mmol) of sodium is added at a temperature in the region of 22° C. under an argon atmosphere to 60 cm³ of methanol. After complete dissolution, 3.6 g (37.5 mmol) of guanidine hydrochloride are added. After stirring at a temperature in the region of 22° C. for 1 hour, the reaction mixture is concentrated to dryness under reduced pressure (2.7 kPa) to give a residue which is suspended in 60 cm³ of 1,2-dimethoxyethane. 2.4 g (7.13 mmol) of 3-chlorocarbonyl-6-methoxy-1-(quinol-4-yl)-1H-indole are subsequently added at a temperature in the region of 22° C. under an argon atmosphere. After stirring at reflux for 18 hours, the reaction mixture is concentrated to dryness under reduced pressure (2.7 kPa) to give a residue which is triturated in 100 cm³ of water. The suspension is filtered and dried to give a beige-coloured powder which is purified by silica gel chromatography [eluent: dichloromethane/methanol (85/15 by volume)]. After concentrating the fractions under reduced pressure (2.7 kPa), 1.7 g of a beige-coloured foam are obtained, which foam is triturated in 60 cm³ of N hydrochloric acid to provide, after filtration, 1.86 g of 3-guanidinocarbonyl-6-methoxy-1-(quinol-4-yl)-1H-indole dihydrochloride in the form of yellow crystals melting at a temperature of greater than 260° C. Mass spectrum (EI): m/e 359 (M⁺·), m/e 301. IR spectrum (KBr): 3356, 2587, 1694, 1630, 1595, 1542, 1495, 1441, 1261, 1232, 1192, 823 and 763 cm⁻¹.

b) 3-Chlorocarbonyl-6-methoxy-1-(quinol-4-yl)-1H-indole 30 cm³ of sulphinyl chloride and one drop of dimethylformamide are added, at a temperature in the region of 22° C. and under an argon atmosphere, to 2.4 g (7.52 mmol) of 3-carboxy-6-methoxy-1-(quinol-4-yl)-1H-indole. After stirring at reflux for 16 hours, the reaction mixture is concentrated to dryness under reduced pressure (2.7 kPa) to give 2.5 g of 3-chlorocarbonyl-6-methoxy-1-(quinol-4-yl)-1H-indole in the form of a yellow solid which is used directly in the following step.

c) 3-Carboxy-6-methoxy-1-(quinol-4-yl)-1H-indole 0.947 g (22.57 mmol) of lithium hydroxide monohydrate and 115 cm³ of water are added at a temperature in the region of 25° C. to 2.5 g (7.52 mmol) of 6-methoxy-3-methoxycarbonyl-1-(quinol-4-yl)-1H-indole dissolved in 115 cm³ of tetrahydrofuran. After stirring at the reflux point of the solvent for 19 hours, the reaction mixture is concentrated under reduced pressure (2.7 kPa) to give a residue which is taken up with 22.5 cm³ of N hydrochloric acid. After filtering off and drying the solid residue at atmospheric pressure at a temperature in the region of 60° C., 2.4 g of 3-carboxy-6-methoxy-1-(quinol-4-yl)-1H-indole are obtained in the form of a beige-coloured solid which decomposes at approximately 175° C.

d) 6-Methoxy-3-methoxycarbonyl-1-(quinol-4-yl)-1H-indole 0.384 g (12 mmol) of sodium hydride, at 75% by mass in liquid petroleum jelly, is added at a temperature in the region of 20° C. under an argon atmosphere to a solution of 2.4 g (11.7 mmol) of 6-methoxy-3-methoxycarbonyl-1H-indole in 60 cm³ of dimethylformamide. After stirring at a temperature in the region of 40° C. for 0.3 hours, 1.98 g (12 mmol) of 4-chloroquinoline are added. After stirring at a temperature in the region of 120° C. for 5 hours, the reaction mixture is poured into 200 cm³ of water and extracted with 200 cm³ of ethyl acetate. The organic phase is washed with 3 times 100 cm³ of water and is then dried over anhydrous magnesium sulphate, filtered and concentrated to dryness under reduced pressure (2.7 kPa) to give 3.9 g of a brown residue which is purified by silica gel chromatography (eluent: cyclohexane/ ethyl acetate (65/35 by volume)]. After concentrating the fractions under reduced pressure, 2.5 g of 6-methoxy-3-methoxycarbonyl-1-(quinol-4-yl)-1H-indole are obtained in the form of a beige-coloured solid melting at 162° C.

e) 6-Methoxy-3-methoxycarbonyl-1H-indole can be obtained by the method described by M. Toyota et al., J. Chem. Soc. Perkin Trans. 1 (1992), (5), 547-552, the content of which is incorporated herein by reference.

EXAMPLE 12 a) 6-Fluoro-3-guanidinocarbonyl-1-(quinol-4-yl)-1H-indole hydrochloride

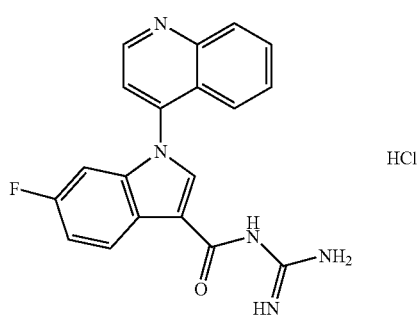

1.35 g (25 mmol) of sodium methoxide are added at 20° C. under an argon atmosphere to a suspension of 2.4 g (25 mmol) of guanidine hydrochloride in 50 cm³ of methanol. After stirring at a temperature in the region of 20° C. for 1 hour, the reaction mixture is concentrated to dryness under reduced pressure (2.7 kPa) to give a residue which is suspended in 40 cm³ of 1,2-dimethoxyethane. 1.62 g (5 mmol) of 3-chlorocarbonyl-6-fluoro-1-(quinol-4-yl)-1H-indole are subsequently added at a temperature in the region of 22° C. under an argon atmosphere. After stirring at reflux for 2 hours, the reaction mixture is concentrated to dryness under reduced pressure (2.7 kPa) to give a residue which is triturated in 100 cm³ of water. The suspension is filtered and dried to give 1.4 g of a beige-coloured powder which is purified by silica gel chromatography [eluent: dichloromethane/methanol (85/15 by volume)]. After concentrating the fractions under reduced pressure (2.7 kPa), 0.435 g of a colourless viscous oil is obtained. The oil is dissolved in 25 cm³ of ethanol and then 3.75 cm³ of N hydrochloric acid are added thereto to provide, after filtering off the precipitate formed, 0.395 g of 6-fluoro-3-guanidinocarbonyl-1-(quinol-4-yl)-1H-indole hydrochloride in the form of yellow crystals melting at a temperature of greater than 260° C. Mass spectrum (EI): m/e 347 (M⁺·), m/e 289. IR spectrum (KBr): 3332, 2586, 1692, 1597, 1543, 1490, 1440, 1259, 1231, 1221, 1182, 902 and 836 cm⁻¹.

b) 3-Chlorocarbonyl-6-fluoro-1-(quinol-4-yl)-1H-indole 20 cm³ of sulphinyl chloride and one drop of dimethylformamide are added at a temperature in the region of 20° C. under an argon atmosphere to 1.39 g (4.53 mmol) of 3-carboxy-6-fluoro-1-(quinol-4-yl)-1H-indole. After stirring at reflux for 1 hour, the reaction mixture is concentrated to dryness under reduced pressure (2.7 kPa) to give 1.7 g of 3-chlorocarbonyl-6-fluoro-1-(quinol-4-yl)-1H-indole in the form of a cream solid which is used directly in the following step.

c) 3-Carboxy-6-fluoro-1-(quinol-4-yl)-1H-indole 0.57 g (13.6 mmol) of lithium hydroxide monohydrate and 70 cm³ of water are added at a temperature in the region of 20° C. to 1.45 g (4.53 mmol) of 6-fluoro-3-methoxycarbonyl-1-(quinol-4-yl)-1H-indole dissolved in 70 cm³ of tetrahydrofuran. After stirring at the reflux point of the solvent for 16 hours, the reaction mixture is concentrated under reduced pressure (2.7 kPa) to give a residue which is taken up with 13.6 cm³ of N hydrochloric acid. After filtering off and drying the solid residue at atmospheric pressure at 60° C., 1.35 g of 3-carboxy-6-fluoro-1-(quinol-4-yl)-1H-indole are obtained in the form of a yellow solid melting at 190° C.

d) 6-Fluoro-3-methoxycarbonyl-1-(quinol-4-yl)-1H-indole 0.25 g (7.8 mmol) of sodium hydride, at 75% by mass in liquid petroleum jelly, is added at a temperature in the region of 20° C. under an argon atmosphere to a solution of 1.5 g (7.76 mmol) of 6-fluoro-3-methoxycarbonyl-1H-indole in 40 cm³ of dimethylformamide. After stirring at a temperature in the region of 40° C. for 0.5 hour, 1.29 g (7.8 mmol) of 4-chloroquinoline are added. After stirring at a temperature in the region of 120° C. for 6 hours, the reaction mixture is poured into 150 cm³ of water and extracted with 150 cm³ of ethyl acetate. The organic phase is washed with 3 times 100 cm³ of water and is then dried over anhydrous magnesium sulphate, filtered and concentrated to dryness under reduced pressure (2.7 kPa) to give a brown solid which is purified by silica gel chromatography [eluent: dichloromethane and then dichloromethane/ethyl acetate (90/10 by volume)]. After concentrating the fractions under reduced pressure, 1.5 g of 6-fluoro-3-methoxycarbonyl-1-(quinol-4-yl)-1H-indole are obtained in the form of a beige-coloured solid melting at 186° C.

e) 6-Fluoro-3-methoxycarbonyl-1H-indole 1.23 g (53.47 mmol) of sodium are added at a temperature in the region of 20° C. under an argon atmosphere to 40 cm³ of methanol. After complete dissolution, 5 g (17.82 mmol) of 6-fluoro-3-trichloroacetyl-1H-indole are added. After stirring at a temperature in the region of 20° C. for 16 hours, the reaction mixture is concentrated to dryness under reduced pressure (2.7 kPa) to give a residue which is taken up with 50 cm³ of demineralised water and extracted with 150 cm³ of ethyl acetate. The organic phase is washed with 3 times 25 cm³ of water and is then dried over anhydrous magnesium sulphate, filtered and concentrated to dryness under reduced pressure (2.7 kPa) to give 3 g of 6-fluoro-3-methoxycarbonyl-1H-indole in the form of a brown solid which is used directly in the following step.

f) 6-Fluoro-3-trichloroacetyl-1H-indole 4.37 g (32.32 mmol) of 6-fluoroindole are added at a temperature in the region of 20° C. under an argon atmosphere to a solution of 4 cm³ (35.55 mmol) of trichloroacetyl chloride in 44.5 cm³ of 1,4-dioxane and 2.9 cm³ (35.55 mmol) of pyridine. After stirring at a temperature in the region of 20° C. for 20 hours, the reaction mixture is poured into 125 cm³ of demineralised water. The precipitate which appears is isolated by filtration, washed with 3 times 20 cm³ of water and then dried at 40° C. under reduced pressure to provide 5 g of 6-fluoro-3-trichloroacetyl-1H-indole in the form of a purple powder melting at 244° C.

EXAMPLE 13 a) 5-Fluoro-3-guanidinocarbonyl-1-(quinol-4-yl)-1H-indole hydrochloride

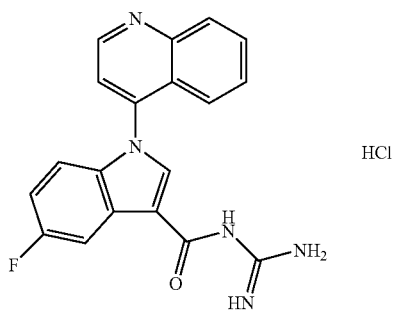

1.62 g (5 mmol) of 3-chlorocarbonyl-5-fluoro-1-(quinol-4-yl)-1H-indole and 1.35 g (25 mmol) of sodium methoxide are added at a temperature in the region of 20° C. under an argon atmosphere to a suspension of 2.4 g (25 mmol) of guanidine hydrochloride in 40 cm³ of 1,2-dimethoxyethane. After stirring at reflux for 2 hours, the reaction mixture is concentrated to dryness under reduced pressure (2.7 kPa) to give a residue which is triturated in 150 cm³ of water. The suspension is filtered and dried to give a beige-coloured powder which is purified by silica gel chromatography [eluent: dichloromethane/methanol (85/15 by volume)]. After concentrating the fractions under reduced pressure (2.7 kPa), 0.243 g of a beige-coloured powder is obtained. The solid is triturated in 10 cm³ N hydrochloric acid for 1.5 hours to provide, after filtration, 0.243 g of a yellow powder. By recrystallization of this solid from aqueous ethanol (comprising 65% water), 0.082 g of 5-fluoro-3-guanidinocarbonyl-1-(quinol-4-yl)-1H-indole hydrochloride is obtained in the form of a yellow powder melting at a temperature of greater than 260° C. Mass spectrum (EI): m/e 347 (M⁺·), m/e 289. IR spectrum (KBr): 3296, 1695, 1511, 1456, 1204 and 767 cm⁻¹.

b) 3-Chlorocarbonyl-5-fluoro-1-(quinol-4-yl)-1H-indole 20 cm³ of sulphinyl chloride and one drop of dimethylformamide are added at a temperature in the region of 20° C. under an argon atmosphere to 1.53 g (5 mmol) of 3-carboxy-5-fluoro-1-(quinol-4-yl)-1H-indole. After stirring at reflux for 1 hour, the reaction mixture is concentrated to dryness under reduced pressure (2.7 kPa) to give 1.8 g of 3-chlorocarbonyl-5-fluoro-1-(quinol-4-yl)-1H-indole in the form of a cream solid which is used directly in the following step.

c) 3-Carboxy-5-fluoro-1-(quinol-4-yl)-1H-indole 0.63 g (15 mmol) of lithium hydroxide monohydrate and 75 cm³ of water are added at a temperature in the region of 20° C. to 1.6 g (5 mmol) of 5-fluoro-3-methoxycarbonyl-1-(quinol-4-yl)-1H-indole dissolved in 75 cm³ of tetrahydrofuran. After stirring at the reflux point of the solvent for 16 hours, the reaction mixture is concentrated under reduced pressure (2.7 kPa) to give a residue which is taken up with 15 cm³ of N hydrochloric acid. After filtering off and drying the solid residue at atmospheric pressure at a temperature in the region of 60° C., 1.44 g of 3-carboxy-5-fluoro-1-(quinol-4-yl)-1H-indole are obtained in the form of a yellow solid melting at approximately 148° C.

d) 5-Fluoro-3-methoxycarbonyl-1-(quinol-4-yl)-1H-indole 0.384 g (12 mmol) of sodium hydride, at 75% by mass in liquid petroleum jelly, is added at a temperature in the region of 20° C. under an argon atmosphere to a solution of 2.26 g.(11.7 mmol) of 5-fluoro-3-methoxycarbonyl-1H-indole in 60 cm³ of dimethylformamide. After stirring at a temperature in the region of 40° C. for 0.5 hour, 1.98 g (12 mmol) of 4-chloroquinoline are added. After stirring at a temperature in the region of 120° C. for 6 hours, the reaction mixture is poured into 200 cm³ of water and extracted with 200 cm³ of ethyl acetate. The organic phase is washed with 3 times 100 cm³ of water and is then dried over anhydrous magnesium sulphate, filtered and concentrated to dryness under reduced pressure (2.7 kPa) to give 3.5 g of a brown solid which is purified by silica gel chromatography (eluent: dichloromethane). After concentrating the fractions under reduced pressure, 1.6 g of 5-fluoro-3-methoxycarbonyl-1-(quinol-4-yl)-1H-indole are obtained in the form of a beige-coloured solid melting at 172° C.

e) 5-Fluoro-3-methoxycarbonyl-1H-indole can be prepared according to WO 00/71537, the content of which is incorporated herein by reference.

EXAMPLE 14 a) 5-Chloro-3-guanidinocarbonyl-1-(quinolin-4-yl)-1H-indole

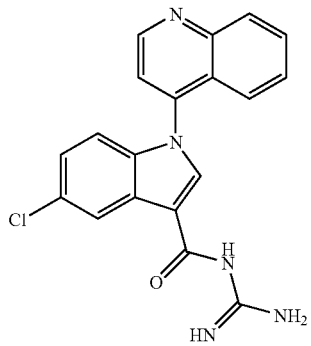

3.11 g (32.55 mmol) of guanidine hydrochloride are added to a solution of 1.76 g (32.55 mmol) of sodium methoxide in 60 cm³ of methanol at a temperature in the region of 20° C. under an argon atmosphere. After stirring at this temperature for 2 hours, the mixture is concentrated to dryness under reduced pressure (2.7 kPa). The residue is taken up in 60 cm³ of 1,2-dimethoxyethane, and 2.46 g (6.51 mmol) of 5-chloro-3-chlorocarbonyl-1-(quinolin-4-yl)-1H-indole hydrochloride are added. After stirring at the reflux temperature of the solvent for 2 hours, the reaction mixture is concentrated to dryness under reduced pressure (2.7 kPa). The residue is triturated in 250 cm³ of water and the suspension is filtered and then dried. The residue is purified by chromatography on silica gel [eluent: dichloromethane/methanol (85/15 by volume)]. After the fractions containing the expected product have been concentrated to dryness under reduced pressure (2.7 kPa), 1.2 g of 5-chloro-3-guanidinocarbonyl-1-(quinolin-4-yl)-1H-indole are obtained in the form of a beige-colored powder melting at a temperature above 260° C. Mass spectrum (CI): m/e 363 (M+H)+)+ (base peak). IR spectrum (KBr): 3466; 3398; 3322; 1636; 1593; 1571; 1510; 1451; 1383; 1356; 1265; 1219; 881; 810; 792; 775 and 649 cm⁻¹.

b) 5-Chloro-3-chlorocarbonyl-1-(quinolin-4-yl)-1H-indole hydrochloride 45 cm³ of sulphinyl chloride and one drop of dimethylformamide are added to 2.1 g (6.51 mmol) of 3-carboxy-5-chloro-1-(quinolin-4-yl)-1H-indole at a temperature in the region of 20° C. under an argon atmosphere. After stirring at reflux for 1 hour, the reaction mixture is concentrated to dryness under reduced pressure (2.7 kPa), giving 2.5 g of 5-chloro-3-chlorocarbonyl-1-(quinolin-4-yl)-1H-indole hydrochloride in the form of a cream-colored solid, which is used directly in the following step.

c) 3-Carboxy-5-chloro-1-(quinolin-4-yl)-1H-indole 0.42 g (15 mmol) of lithium hydroxide monohydrate and 50 cm³ of water are added to 1.13 g (3.35 mmol) of 5-chloro-3-methoxycarbonyl-1-(quinolin-4-yl)-1H-indole dissolved in 50 cm³ of tetrahydrofuran at a temperature in the region of 20° C. After stirring for 16 hours at the reflux temperature of the solvent, the reaction mixture is concentrated to dryness under reduced pressure (2.7 kPa). The residue is taken up in 10 cm³ of 1N hydrochloric acid, the suspension is then filtered, and the solid residue is dried under atmospheric pressure at a temperature in the region of 60° C., giving 0.95 g of 3-carboxy-5-chloro-1-(quinolin-4-yl)-1H-indole in the form of a cream-colored solid, which is used directly in the following step.

d) 5-Chloro-3-methoxycarbonyl-1-(quinolin-4-yl)-1H-indole 0.771 g (24 mmol) of sodium hydride at 75% by weight in liquid petroleum jelly is added to a solution of 5.03 g (24 mmol) of 5-chloro-3-methoxycarbonyl-1H-indole in 120 cm³ of dimethylformamide at a temperature in the region of 20° C. under an argon atmosphere. After the reaction mixture has been stirred for 0.5 hour at a temperature in the region of 40° C., 3.94 g (24 mmol) of 4-chloroquinoline are added. After stirring for 6 hours at a temperature in the region of 120° C., the reaction mixture is cooled to a temperature in the region of 20° C. and then poured into 400 cm³ of water and extracted with 500 cm³ of ethyl acetate. The organic phase is washed three times with 250 cm³ of water, dried over anhydrous magnesium sulphate, filtered and then concentrated to dryness under reduced pressure (2.7 kPa). The residue is purified by chromatography on silica gel (eluent: dichloromethane). After the fractions containing the expected product have been concentrated to dryness under reduced pressure, 2.5 g of 5-chloro-3-methoxycarbonyl-1-(quinolin-4-yl)-1H-indole are obtained in the form of a sticky beige-colored solid, which is used in the following step without further purification.

e) 5-Chloro-3-methoxycarbonyl-1H-indole can be prepared according to WO 95/22524, the content of which is incorporated herein by reference.

EXAMPLE 15 a) N-[1-(Cinnolin-4-yl)-1H-indole-3-carbonyl]-guanidine trifluoroacetate

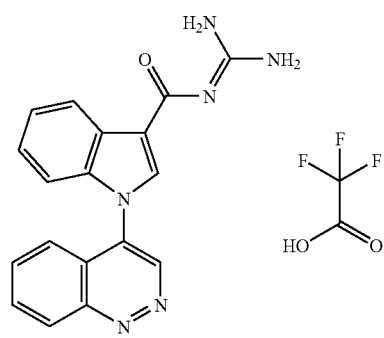

A solution of guanidine is prepared by stirring 5 mmol (560 mg) of potassium t-butoxide and 5.5 mmol (525 mg) of guanidine hydrochloride in 5 ml of dry DMF for 30 minutes at room temperature under exclusion of moisture. To the resulting suspension is added the methyl ester obtained below, the mixture is stirred for 18 h at room temperature under argon. The mixture is filtered and the filtrate directly subjected to purification by prep. HPLC (acetonitrile/H₂O+0.1% trifluoroactetic acid) to yield N-[1-(cinnolin-4-yl)-1H-indole-3-carbonyl]-guanidine trifluoroacetate as a foam.

The product was characterized by analytical HPLC/MS (Waters 1525 HPLC with. Micromass MUX-LCT MS detector; column Merck-Purospher 55*2 mm, 3μ RP18; column temperature: room temperature; gradient ($H_2O$+0.1% formic acid):(acetonitrile+0.1% formic acid) from 95:5 (0 min) to 5:95 (5 min) to 5:95 (7 min)).

Retention time: 2.28 min, MS molpeak 331 (M+H, electrospray ionization)

b) 1-(Cinnolin-4-yl)-1H-indole-3-carboxylic acid methyl ester 1 mmol (175 mg) of 1H-indole-3-carboxylic acid methyl ester, 1.1 mmol (181 mg) of 4-chloro-cinnoline and 1.2 mmol (390 mg) of $Cs_2CO_3$ are suspended in 3 ml of dry DMF. The mixture is stirred for 60 h at 80° C. under argon, allowed to cool to room temperature, and diluted with water (20 ml). Part of the product precipitates and is filtered off, the filtrate is extracted twice with ethyl acetate (20 ml portions). The combined extracts are dried over anhydrous $Na_2SO_4$ and evaporated. The residue is combined with the precipitate and purified by prep. HPLC to yield 1-(cinnolin-4-yl)-1H-indole-3-carboxylic acid methyl ester (MS molpeak 304 (M+H, electrospray ionization)) as an off-white foam after freeze-drying.

The following compound was prepared in analogy to example 15:

cells, the fluorescence intensity of which depends on the $pH_i$, and on the $NH_4Cl$, which results in a slight basification of the cells.

The precursor BCECF-AM, a non-fluorescent dye, is, as an ester, capable of crossing the membrane. The actual dye, which is incapable of crossing the membrane, is released inside the cell by esterases.

After this 20-minute incubation, the loading buffer, which comprises $NH_4Cl$ and free BCECF-AM, is removed by washing three times in the cell washing device (Tecan Columbus), each wash being performed with 400 μl of washing buffer (133.8 mM of choline chloride, 4.7 mM of KCl, 1.25 mM of $MgCl_2$, 1.25 mM of $CaCl_2$, 0.97 mM of $K_2HPO_4$, 0.23 mM of $KH_2PO_4$, 5 mM of HEPES and 5 mM of glucose; pH 7.4 (adjusted with KOH)). The residual volume remaining in the wells is 90 μl (possibly between 50 and 125 μl). This washing step removes the free BCECF-AM and results in an intracellular acidification ($pH_i$ of 6.3-6.4) due to the removal of the external ammonium ions.

As the equilibrium of the intracellular ammonium with the aqueous ammonia and the protons, by removal of the extracellular ammonium and by the subsequent immediate crossing of the aqueous ammonia across the cell membrane, is disrupted, the washing process results in intracellular protons

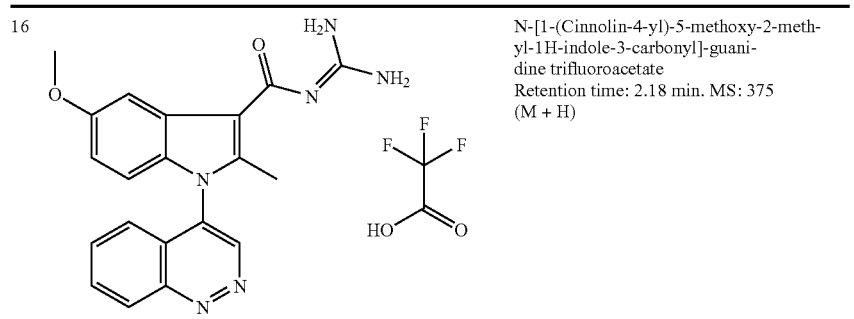

16

N-[1-(Cinnolin-4-yl)-5-methoxy-2-methyl-1H-indole-3-carbonyl]-guanidine trifluoroacetate
Retention time: 2.18 min. MS: 375 (M + H)

NHE Inhibition Method

The NHE inhibitory activities ($IC_{50}$ values) of the compounds according to the invention were determined by a FLIPR test.

The test is performed in the FLIPR (Fluorescent Imaging Plate Reader) equipped with clear-bottomed and black-walled 96-well microtitration plates. The transfected cell lines expressing the various NHE subtypes (the parental cell line LAP-1 shows no endogenous NHE activity as a result of mutagenesis and subsequent selection) are seeded the preceding day at a density of ~25 000 cells/well.

The growth medium for the transfected cells (Iscove+10% foetal calf serum) also comprises G418 as selection antibiotic to ensure the presence of transfected sequences.

The actual test begins by eliminating the growth medium and adding 100 μl of loading buffer per well (5 μM of BCECF-AM [2',7'-bis(2-carboxyethyl)-5-(6)-carboxyfluoresceine acetoxymethyl ester] in 20 mM of $NH_4Cl$ 115 mM of choline chloride, 1 mM of $CaCl_2$, 5 mM of KCl, 20 mM of HEPES and 5 mM of glucose; pH 7.4 (adjusted with KOH). The cells are then incubated for 20 minutes at 37° C. This incubation results in the loading of the fluorescent dye into the remaining, which is the cause of the intracellular acidification. This acidification can result finally in the death of the cells if it lasts long enough. It is important here for the washing buffer to be free of sodium (<1 mM), otherwise the extracellular sodium ions would result in an immediate increase in the $pH_i$ on account of the activity of the cloned NHE isoforms. It is also important for all the buffers used (loading buffer, washing buffer and regeneration buffer) not to contain any $HCO_3$-ions, otherwise the presence of bicarbonate would result in the activation of bicarbonate-dependent systems that disrupt the $pH_i$ regulation, which systems are contained in the LAP-1 parental cell line.

The microtiter plates containing acidified cells are then transferred (up to 20 minutes after the acidification) to the FLIPR. In the FLIPR, the intracellular fluorescent dye is activated with light of a wavelength of 488 nm, which is generated by an argon laser, and the measuring parameters (laser power, illumination time and diaphragm of the CDD camera integrated into the FLIPR) are chosen such that the average value of the fluorescent signal per well is between 30,000 and 35,000 relative fluorescence units.

The actual measurement in the FLIPR starts with a photograph being taken by the CCD camera every two seconds under software control. After 10 seconds, the increase in the intracellular pH is initiated by adding 90 μl of regeneration buffer (133.8 mM of NaCl, 4.7 mM of KCl, 1.25 mM of $MgCl_2$, 1.25 mM of $CaCl_2$, 0.97 mM of $K_2HPO_4$, 0.23 mM of $KH_2PO_4$, 10 mM of HEPES and 5 mM of glucose; pH 7.4 (adjusted with NaOH)) using a 96-well pipette device incorporated into the FLIPR. Some wells, to which is added pure regeneration buffer, serve as positive controls (100% NHE activity). The negative controls (0% NHE activity) contain washing buffer. Regeneration buffer with twice the concentration of test substance is added to all the other wells. Measurement in the FLIPR terminates after 60 measurements (two minutes).

The experimental data allow the NHE activities to be calculated for each concentration of test substance and, from these, the $IC_{50}$ values of the substances. For the NHE1 subtype the following results are obtained.

| example No. | IC50 (NHE1)/µM |
|---|---|
| 1 | 0.014 |
| 2 | 0.004 |
| 3 | 0.535 |
| 4 | 0.200 |
| 5 | 4.98 |
| 6 | 0.206 |
| 7 | 0.433 |
| 8 | 0.143 |
| 9 | 0.275 |
| 10 | 1.87 |
| 11 | 0.047 |
| 12 | 0.076 |
| 13 | 0.039 |
| 14 | 2.46 |
| 15 | 0.0015 |
| 16 | 1.67 |

The invention relates also to the use of the compounds of the formula I and/or pharmaceutically acceptable salts thereof for the preparation of medicaments and pharmaceutical compositions as inhibitors of the NHE. Claimed is a medicine for human, veterinary or phytoprotective use, comprising an effective amount of a compound of the formula I and/or the pharmaceutically acceptable salts thereof, together with pharmaceutically acceptable carriers and additives, alone or in combination with other active pharmaceutical ingredients or medicaments. The pharmaceutical compositions according to the invention consist of a compound of the formula I and/or the pharmaceutically acceptable salt thereof, in pure form or in the form of a composition in which it is combined with any other pharmaceutically compatible product, which may be inert or physiologically active. The medicaments according to the invention can be administered, for example, orally, parenterally, intravenously, rectally, transdermally, topically or by inhalation. The medicaments generally comprise active ingredients of the formula I and/or pharmaceutically acceptable salts thereof in an amount of from 0.001 mg to 1 g per dose unit.

The excipients suitable for the desired pharmaceutical formulation are familiar to the skilled worker on the basis expert knowledge. Besides solvents, gel formers, suppository bases, tablet excipients, and other active ingredient carriers, it is possible to use, for example, antioxidants, dispersants, emulsifiers, antifoams, flavourings, preservatives, solubilizers or colors.

For a pharmaceutical formulation for oral administration, the active compounds are mixed with additives suitable for this purpose, such as carriers, stabilizers or inert diluents, and converted by conventional methods into suitable dosage forms such as tablets, coated tablets, hard gelatin capsules, aqueous, alcoholic or oily solutions. Examples of inert carriers which can be used are gum arabic, magnesia, magnesium carbonate, potassium phosphate, lactose, glucose or starch, especially corn starch. It is moreover possible for the preparation to take place both as dry granules and as wet granules. Examples of suitable oily carriers or solvents are vegetable or animal oils such as sunflower oil or fish liver oil.

Tablets, pills, powders (gelatine capsules or cachets) or granules can be used as solid compositions for oral administration. In these compositions, the active principle according to the invention is mixed with one or more inert diluents, such as starch, cellulose, sucrose, lactose or silica, under a stream of argon. These compositions may also comprise substances other than diluents, for example one or more lubricants, such as magnesium stearate or talc, a colorant, a coating (dragees) or a varnish. Pharmaceutically acceptable solutions, suspensions, emulsions, syrups and elixirs comprising inert diluents, such as water, ethanol, glycerol, plant oils or liquid paraffin, can be used as liquid compositions for oral administration. These compositions may comprise substances other than diluents, for example wetting products, sweeteners, thickeners, flavourings or stabilisers.

The sterile compositions for parenteral administration may preferably be aqueous or non-aqueous solutions, suspensions or emulsions. Solvents or vehicles that can be used include water, propylene glycol, a polyethylene glycol, plant oils, in particular olive oil, injectable organic esters, for example ethyl oleate, or other suitable organic solvents. These compositions may also comprise adjuvants, in particular wetting agents, tonicity agents, emulsifiers, dispersants and stabilisers. The sterilisation may be performed in several ways, for example by aseptic filtration, by incorporating sterilising agents into the composition, by irradiation or by heating. They may also be prepared in the form of sterile solid compositions that may be dissolved at the time of use in sterile water or any other injectable sterile medium.

The compositions for rectal administration are suppositories or rectal capsules that comprise, besides the active product, excipients, such as cocoa butter, semi-synthetic glycerides or polyethylene glycols.

The compositions for topical administration may be, for example, creams, lotions, eye drops, mouthwashes, nasal drops or aerosols.

For subcutaneous, intramuscular or intravenous administration, the active compounds used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

Suitable as pharmaceutical formulation for administration in the form of aerosols or sprays are, for example, solutions, suspensions or emulsions of the active ingredient of the formula I and/or the pharmaceutically acceptable salts thereof in a pharmaceutically acceptable solvent such as, in particular, ethanol or water, or a mixture of such solvents. The formulation may, if required, also contain other pharmaceutical excipients such as surfactants, emulsifiers and stabilizers, and a propellant gas. Such a preparation contains, for example, the active ingredient in a concentration of about 0.1 to 10, in particular of about 0.3 to 3% by weight.

The dosage of the active ingredient of the formula I to be administered, and the frequency of administration, depend on the desired effect, the potency and duration of action of the compounds used; additionally also on the nature and severity of the disorder to be treated and on the sex, age, weight and individual responsiveness of the mammal to be treated. In general, the doctor will determine the appropriate dosage as a function of the age and weight and all the other factors specific to the individual to be treated.

On average, the daily dose of a compound of the formula I and/or the pharmaceutically acceptable salts thereof for a patient weighing about 75 kg is at least 0.001 mg/kg, preferably 1 mg/kg, to a maximum of 1000 mg/kg, preferably 100 mg/kg, of body weight. For acute episodes of the disorder, for example immediately after suffering a myocardial infarction, higher and, in particular, more frequent dosages may also be necessary, e.g. up to 4 single doses a day. Up to 2000 mg a day may be necessary, in particular on i.v. administration, for example for a patient with infarction in the intensive care unit, and the compounds of the invention can be administered by infusion.

The following examples illustrate compositions according to the invention:

EXAMPLE A

Gel capsules containing a 50 mg dose of active product, having the composition below, can be prepared according to the usual technique:

| | |
|---|---|
| Compound of the formula (I) | 50 mg |
| Cellulose | 18 mg |
| Lactose | 55 mg |
| Colloidal silica | 1 mg |
| Sodium carboxymethyl starch | 10 mg |
| Talc | 10 mg |
| Magnesium stearate | 1 mg |

EXAMPLE B

Tablets comprising a 50 mg dose of active product, having the composition below, can be prepared according to the usual technique:

| | |
|---|---|
| Compound of the formula (I) | 50 mg |
| Lactose | 104 mg |
| Cellulose | 40 mg |
| Polyvidone | 10 mg |
| Sodium carboxymethyl starch | 22 mg |
| Talc | 10 mg |
| Magnesium stearate | 2 mg |
| Colloidal silica | 2 mg |
| Mixture of hydroxymethylcellulose, glycerol and titanium oxide (72/3.5/24.5) qs 1 finished film-coated tablet weighing | 245 mg |

EXAMPLE C

An injectable solution comprising 10 mg of active product, having the composition below, can be prepared:

| | | |
|---|---|---|
| Compound of the formula (I) | 10 | mg |
| Benzoic acid | 80 | mg |
| Benzyl alcohol | 0.06 | ml |
| Sodium benzoate | 80 | mg |
| 95% ethanol | 0.4 | ml |
| Sodium hydroxide | 24 | mg |
| Propylene glycol | 1.6 | ml |
| Water | qs 4 | ml |

What is claimed is:

1. A compound of the formula (I)

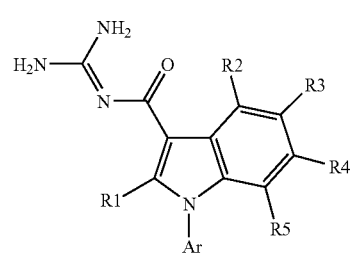

wherein,
R1 is hydrogen or alkyl having 1, 2, 3, 4, 5 or 6 carbon atoms,
R2 is hydrogen, alkyl having 1, 2, 3, 4, 5 or 6 carbon atoms, halogen, NRaRb or polyfluoroalkyl having 1, 2, 3 or 4 carbon atoms,
Ra and Rb
  are independently of each other hydrogen, linear or branched alkyl having 1, 2, 3, 4, 5 or 6 carbon atoms or Ra and Rb form, together with the nitrogen atom to which they are attached, a 5- or 6-membered heterocycle, which may optionally contain another hetero atom chosen from O, S and N,
R3 is hydrogen, alkyl having 1, 2, 3, 4, 5 or 6 carbon atoms, halogen, alkoxy having 1, 2, 3, 4, 5 or 6 carbon atoms or hydroxyl,
R4 is hydrogen, alkyl having 1, 2, 3, 4, 5 or 6 carbon atoms, halogen, alkoxy having 1, 2, 3, 4, 5 or 6 carbon atoms or hydroxyl,
R5 is hydrogen or halogen,
Ar is a 9- or a 10-membered bicyclic heteroaryl having one, two or three nitrogen atoms,
which may be linked via any of its positions, or a racemic mixture, enantiomer, diastereomer, or tautomer of such compound, or a mixture thereof, or a pharmaceutically acceptable salt of such compound, racemic mixture, enantiomer, diastereomer, tautomer, or mixture.

2. A compound according to claim 1, wherein
R1 is hydrogen or alkyl having 1, 2, 3, 4, 5 or 6 carbon atoms,
R2 is hydrogen, alkyl having 1, 2, 3, 4, 5 or 6 carbon atoms, halogen, NRaRb or polyfluoroalkyl having 1, 2, 3 or 4 carbon atoms,
Ra and Rb are independently of each other hydrogen, linear or branched alkyl having 1, 2, 3, 4, 5 or 6 carbon atoms or Ra and Rb form, together with the nitrogen atom to which they are attached, a 5- or 6-membered heterocycle, which may optionally contain another hetero atom chosen from O, S and N,
R3 is hydrogen, alkyl having 1, 2, 3, 4, 5 or 6 carbon atoms, halogen, alkoxy having 1, 2, 3, 4, 5 or 6 carbon atoms or hydroxyl,
R4 is hydrogen, alkyl having 1, 2, 3, 4, 5 or 6 carbon atoms, halogen, alkoxy having 1, 2, 3, 4, 5 or 6 carbon atoms or hydroxyl,
R5 is hydrogen or halogen,
Ar is quinoline, isoquinoline, cinnoline or 7H-pyrrolo-[2,3-d]-pyrimidine, which may be linked via any of its positions.

3. A compound according to claim 1 wherein
R1 is hydrogen or alkyl having 1, 2, 3, 4, 5 or 6 carbon atoms,
R2 is hydrogen, alkyl having 1, 2, 3, 4, 5 or 6 carbon atoms, halogen, NRaRb or polyfluoroalkyl having 1, 2, 3, 4, 5 or 6 carbon atoms,
Ra and Rb
are independently of each other hydrogen, linear or branched alkyl having 1, 2, 3, 4, 5 or 6 carbon atoms or Ra and Rb form, together with the nitrogen atom to which they are attached, a 5- or 6-membered heterocycle, which may optionally contain another hetero atom chosen from O, S and N,
R3 is hydrogen, alkyl having 1, 2, 3, 4, 5 or 6 carbon atoms, halogen, alkoxy having 1, 2, 3, 4, 5 or 6 carbon atoms or hydroxyl,
R4 is hydrogen, alkyl having 1, 2, 3, 4, 5 or 6 carbon atoms, halogen, alkoxy having 1, 2, 3, 4, 5 or 6 carbon atoms or hydroxyl,
R5 is hydrogen or halogen,
Ar is quinoline, which may be linked via any of its positions.

4. A compound according to claim 1 wherein
R1 is hydrogen or alkyl having 1, 2, 3, 4, 5 or 6 carbon atoms,
R2 is hydrogen, alkyl having 1, 2, 3, 4, 5 or 6 carbon atoms, halogen, NRaRb or polyfluoroalkyl having 1, 2, 3, 4, 5 or 6 carbon atoms,
Ra and Rb
are independently of each other hydrogen, linear or branched alkyl having 1, 2, 3, 4, 5 or 6 carbon atoms or Ra and Rb form, together with the nitrogen atom to which they are attached, a 5- or 6-membered heterocycle, which may optionally contain another hetero atom chosen from O, S and N,
R3 is hydrogen, alkyl having 1, 2, 3, 4, 5 or 6 carbon atoms, halogen, alkoxy having 1, 2, 3, 4, 5 or 6 carbon atoms or hydroxyl,
R4 is hydrogen, alkyl having 1, 2, 3, 4, 5 or 6 carbon atoms, halogen, alkoxy having 1, 2, 3, 4, 5 or 6 carbon atoms or hydroxyl,
R5 is hydrogen or halogen,
Ar is isoquinoline, which may be linked via any of its positions.

5. A compound according to claim 1 which is:
3-guanidinocarbonyl-1-(isoquinol-1-yl)-1H-indole,
3-guanidinocarbonyl-1-(quinol-4-yl)-1H-indole,
3-guanidinocarbonyl-1-(quinol-2-yl)-1H-indole,
3-guanidinocarbonyl-1-(isoquinol-1-yl)-5-methyl-1H-indole,
3-guanidinocarbonyl-5-methyl-1-(quinol-2-yl)-1H-indole,
3-guanidinocarbonyl-5-methyl-1-(quinol-4-yl)-1H-indole,
3-guanidinocarbonyl-1-(quinol-3-yl)-1H-indole,
3-guanidinocarbonyl-1-(quinol-6-yl)-1H-indole,
3-guanidinocarbonyl-1-(quinol-8-yl)-1H-indole,
3-guanidinocarbonyl-1-(isoquinol-3-yl)-1H-indole,
3-guanidinocarbonyl-6-methoxy-1-(quinol-4-yl)-1H-indole,
3-guanidinocarbonyl-6-hydroxy-1-(quinol-4-yl)-1H-indole,
6-fluoro-3-guanidinocarbonyl-1-(quinol-4-yl)-1H-indole,
5-fluoro-3-guanidinocarbonyl-1-(quinol-4-yl)-1H-indole,
4-chloro-3-guanidinocarbonyl-1-(quinol-4-yl)-1H-indole,
5-chloro-3-guanidinocarbonyl-1-(quinol-4-yl)-1H-indole,
6-chloro-3-guanidinocarbonyl-1-(quinol-4-yl)-1H-indole,
4-fluoro-3-guanidinocarbonyl-1-(quinol-4-yl)-1H-indole,
3-guanidinocarbonyl-4-methyl-1-(quinol-4-yl)-1H-indole,
3-guanidinocarbonyl-4-trifluoromethyl-1-(quinol-4-yl)-1H-indole,
4-dimethylamino-3-guanidinocarbonyl-1-(quinol-4-yl)-1H-indole,
3-guanidinocarbonyl-1-(cinnolin-4-yl)-1H-indole, or
5-methoxy-3-guanidinocarbonyl-1-(cinnolin-4-yl)-1H-indole,
or a tautomer thereof or a pharmaceutically acceptable salt of such compound or tautomer.

6. A pharmaceutical composition for human, veterinary, or phytoprotective use comprising an effective amount of a compound according to claim 1 together with a pharmaceutically acceptable medium.

7. A process for the preparation of a compound according to claim 1 comprising the following steps:

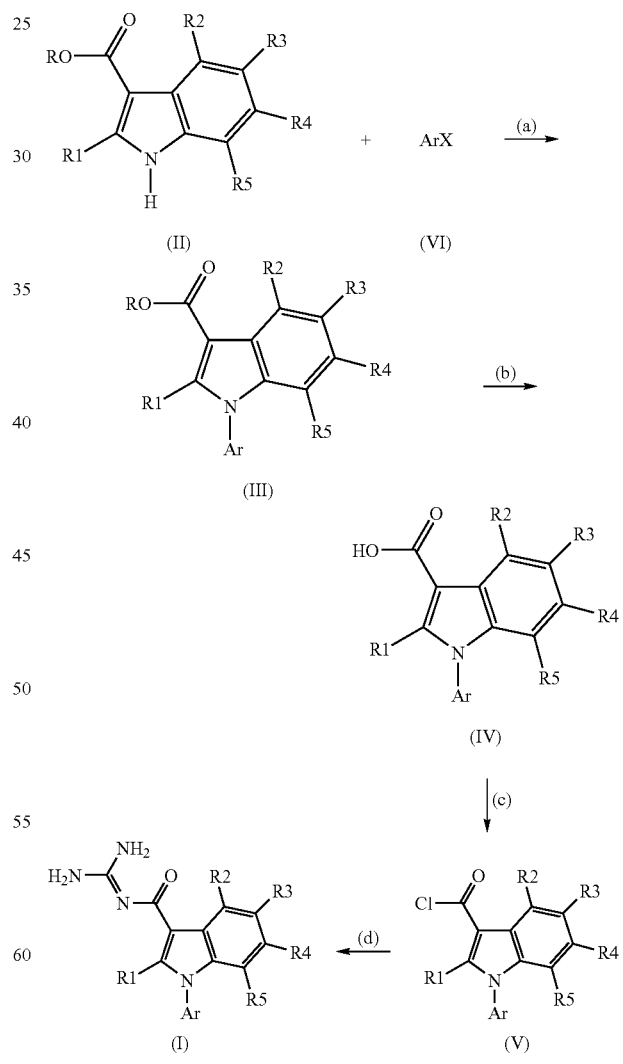

a) reacting a heteroaryl halide ArX of the formula (VI) with a 3-alkoxycarbonyl-1H-indole of the formula (II);

b) saponifying the obtained 3-alkoxycarbonyl-1-heteroaryl-indole of the formula (III);
c) converting the 3-carboxy-1-heteroaryl-indole of the formula (IV) in the acid chloride of formula (V);
d) reacting the obtained product of formula (V) with guanidine, the product is isolated and is optionally converted into a pharmaceutically acceptable salt, wherein in the compounds of the formula II, III, IV, V and VI Ar, R1, R2, R3, R4 and R5 are defined as in claim 1, X is F, Cl, Br or I and R is alkyl having 1, 2, 3, 4, 5 or 6 carbon atoms.

\* \* \* \* \*